US009447097B2

(12) United States Patent
Hoves et al.

(10) Patent No.: US 9,447,097 B2
(45) Date of Patent: Sep. 20, 2016

(54) 4-AMINO-IMIDAZOQUINOLINE COMPOUNDS

(71) Applicant: Hoffmann-La Roche Inc., Little Falls, NJ (US)

(72) Inventors: Sabine Hoves, Schlossbergstrasse (DE); Bernd Kuhn, Reinach (CH); Fabienne Ricklin, Hombourg (FR); Stephan Roever, Inzlingen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/093,481

(22) Filed: Apr. 7, 2016

(65) Prior Publication Data

US 2016/0222010 A1 Aug. 4, 2016

Related U.S. Application Data

(62) Division of application No. 14/692,968, filed on Apr. 22, 2015, now Pat. No. 9,334,268.

(30) Foreign Application Priority Data

Apr. 22, 2014 (EP) .................................... 14165349

(51) Int. Cl.
*C07D 471/04* (2006.01)
*A61K 31/4188* (2006.01)
*A61K 31/437* (2006.01)

(52) U.S. Cl.
CPC .................................. *C07D 471/04* (2013.01)

(58) Field of Classification Search
None
See application file for complete search history.

(56) References Cited

U.S. PATENT DOCUMENTS

2003/0187016 A1 10/2003 Crooks et al.
2013/0202629 A1 8/2013 Carson et al.

FOREIGN PATENT DOCUMENTS

WO 92/15582 A1 9/1992
WO 2005/076783 A2 8/2005
WO 2007/024612 A2 3/2007
WO 2009/111337 A1 9/2009
WO 2010/054215 A1 5/2010
WO 2010/093436 A2 8/2010
WO 2011/017611 A1 2/2011
WO 2011/068233 A1 6/2011
WO 2011/139348 A2 11/2011
WO 2012/045090 A2 4/2012
WO 2012/066336 A1 5/2012
WO 2012/167801 A1 12/2012
WO 2013/033345 A1 3/2013
WO 2013/067597 A1 5/2013
WO 2013/166110 A1 11/2013

OTHER PUBLICATIONS

Written Opinion for PCT/EP2015/058465.
International Search Report for PCT/EP2015/058465, dated May 26, 2015.
Kawai et al., "The Role of Pattern-Recognition Receptors in Innate Immunity: Update on Toll-Like Receptors" Nature Immunology 11(5):373-384 (May 2010).
Uematsu et al., "Toll-Like Receptors and Type I Interferons" Journal of Biological Chemistry 282(21):15319-15323 (May 25, 2007).
Hennessey et al., "Targeting Toll-Like Receptors: Emerging Therapeutics?" Nature Reviews: Drug Discovery 9:293-307 (Apr. 2010).
Kawai et al., "Toll-Like Receptors and Their Crosstalk with Other Innate Receptors in Infection and Immunity" Immunity 34:637-650 (May 27, 2011).
Holldack, "Toll-Like Receptors as Therapeutic Targets for Cancer" Drug Discovery Today 19(4):379-382 (Apr. 2014).

*Primary Examiner* — Timothy R Rozof

(57) ABSTRACT

This invention relates to novel 4-amino-imidazoquinoline compounds of the formula

I

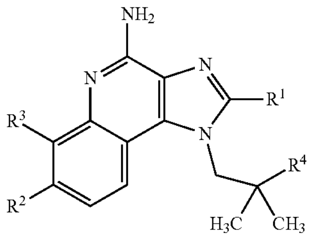

wherein $R^1$ to $R^4$ are as defined in the description and in the claims, as well as pharmaceutically acceptable salts thereof. These compounds are TLR agonists and may therefore be useful as medicaments for the treatment of diseases such as cancer or infectious diseases.

14 Claims, No Drawings

4-AMINO-IMIDAZOQUINOLINE COMPOUNDS

CROSS-REFERENCE TO RELATED APPLICATIONS

This application is a divisional application of U.S. patent application Ser. No. 14/692,968, filed Apr. 22, 2015, which claims the benefit of the filing date of European Patent Application No. 14165349.3, filed Apr. 22, 2014, the contents of which applications are hereby incorporated by reference in their entirety.

FIELD OF THE INVENTION

The present invention relates to novel 4-amino-imidazoquinoline derivatives having pharmaceutical activity, their manufacture, pharmaceutical compositions containing them and their potential use as medicaments.

In particular, the present invention relates to compounds of the formula

I

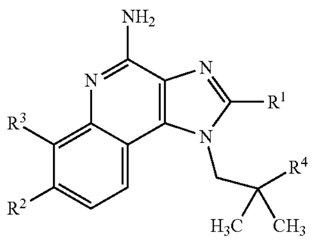

wherein $R^1$ to $R^4$ and X are as described below, or to pharmaceutically acceptable salts thereof.

The compounds are TLR agonists. In particular, the compounds are TLR7 and/or TLR8 agonists and more particularly agonists of both TLR7 and TLR8 receptors. Thus, they may be useful for the treatment and prevention of cancer, autoimmune and infectious diseases. For example, they may be useful in a vaccination against diseases such as cancer, autoimmune or infectious diseases.

BACKGROUND OF THE INVENTION

Toll-like receptors (TLRs) are a family of membrane-spanning receptors that are expressed on cells of the immune system like dendritic cells, macrophages, monocytes, T cells, B cells, NK cells and mast cells but also on endothelial and epithelial cells (Kawai et al., Immunity, 2011, 34, 637-650, Kawai et al., Nat. Immunol., 2010, 11, 373-384). TLRs that recognize bacterial and fungal components are expressed on the cell surface (i.e. TLR1, 2, 4, 5 and 6), while others that recognize viral or microbial nucleic acids like TLR3, 7, 8 and 9 are localized to the endolysosomal/phagosomal membrane (Henessy et al. Nat. Rev. Drug Discovery 2010, 9, 293-307). TLR activation leads to the induction and release of pro-inflammatory cytokines, with the specific activation sequence and response depending on the specific TLR and cell type. TLR7 and TLR8 are both expressed in monocytes and macrophages, with TLR7 also highly expressed in plasmacytoid dendritic cells and TLR8 in myeloid dendritic cells and mast cells. Both receptors are activated by ssRNA and their activation stimulates the production of cytokines such as IL-6, IL-12, TNF-α and IFN-γ and additional co-stimulatory molecules and chemokine receptors. Dependent on the cell type, type I interferons, IFNα (from plasmacytoid dendritic cells) and IFNβ, are also produced by cells upon activation with TLR7/8 agonists (Uematsu et al., J. Biol. Chem., 2007, 282, 15319-15323).

Small molecule agonists for both the TLR7 and TLR8 receptor as well as analogs modified for use as vaccine adjuvants or conjugates have been identified in many patents (i.e. WO1992015582, US 2003187016, WO 2005076783, WO2007024612, WO2009111337, WO2010093436, WO2011017611, WO2011068233, WO2011139348, WO2012066336, WO2012167081, WO2013033345, WO 2013067597, WO2013166110, and US2013202629). Clinical experience has been obtained using exclusively TLR7 agonists. A number of the early compounds have demonstrated anti-viral and anti-cancer properties. For example, the TLR7 agonist imiquimod (ALDARA™) was approved by the U.S. Food and Drug Administration as a topical agent for the treatment of genital warts, superficial basal cell carcinoma and actinic keratosis. Systemic application however of the early TLR7 agonists like resiquimod has been abandoned due to intolerable cardiotoxicity observed upon global chemokine stimulation at therapeutic levels (Holldack, Drug Discovery Today, 2013, 1-4). Knowledge about TLR8 agonists is less advanced and mostly restricted to data with early mixed TLR7/8 agonists like resiquimod and more recently to compounds described by VentiRX Pharmaceuticals (i.e. WO2010054215, WO2012045090). At present there is still a need for additional small molecule TLR7 and TLR8 agonists, specifically those with improved potency.

The present invention is directed to 1H-imidazo[4,5-c]quinolin-4-amine-2-methylpropan-2-yloxy derivatives with improved cellular potency over known TLR7 and/or TLR8 agonists of this type for use in the treatment of cancer, preferably solid tumors and lymphomas, and for other uses including the treatment of certain skin conditions or diseases, such as atopic dermatitis, the treatment of infectious diseases, preferably viral diseases, and for use as adjuvants in vaccines formulated for use in cancer therapy or by desensitizing of the receptors by continuous stimulation in the treatment of autoimmune diseases.

Specifically, the present invention discloses 1H-imidazo[4,5-c]quinolin-4-amine-2-methylpropan-2-yloxy derivatives that are derivatized directly on the tertiary alcohol with an aminoethyl or glycine moiety. Due to the poor reactivity of the tertiary alcohol these derivatives had obviously eluded earlier attempts at synthesis. Surprisingly, these new compounds possess high cellular potency at TLR7 that is comparable or even better than resiquimod itself, whereas close analogs that have been described earlier such as 1-(2-(2-Aminoethoxy)ethyl)-2-(ethoxymethyl)-1H-imidazo[4,5-c]quinolin-4-amine (Example 69 of US20030187016) do not show the required activity. In addition and also surprisingly, the described 1H-imidazo[4,5-c]quinolin-4-amine-2-methylpropan-2-yloxy derivatives are strong TLR8 receptor agonists with potency comparable or superior to so far disclosed TLR8 agonists from other chemical classes and much improved over resiquimod itself. Thus, the compounds of the present invention fulfil the need of activating both TLR7 and TLR8 receptors with improved potency.

SUMMARY OF THE INVENTION

The present invention relates to 4-amino-imidazoquinoline derivatives of the formula

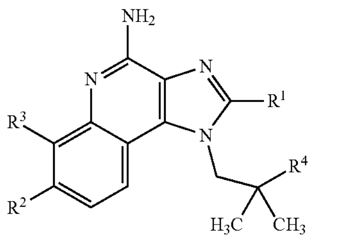

I wherein $R^1$ is $C_{1-7}$-alkyl or $C_{1-7}$-alkoxy-$C_{1-7}$-alkyl;

$R^2$ is selected from the group consisting of hydrogen, halogen, hydroxyl, hydroxy-$C_{1-7}$-alkyl, alkoxy-$C_{1-7}$-alkyl, carboxyl, carboxyl-$C_{1-7}$-alkyl, carboxyl-$C_{2-7}$-alkenyl, aminocarbonyl-$C_{1-7}$-alkyl, aminocarbonyl-$C_{2-7}$-alkenyl, $C_{1-7}$-alkylamino-carbonyl-$C_{1-7}$-alkyl, $C_{1-7}$-alkylamino-carbonyl-$C_{2-7}$-alkenyl, $C_{1-7}$-alkoxy-carbonyl-$C_{1-7}$-alkyl, $C_{1-7}$-alkoxycarbonyl-$C_{2-7}$-alkenyl, $C_{1-7}$-alkyl-sulfonyl-$C_{1,7}$-alkyl, sulfamoyl-$C_{1-7}$-alkyl, $C_{1-7}$-alkyl-sulfamoyl-$C_{1-7}$-alkyl, phenyl, said phenyl being unsubstituted or substituted with one, two or three groups selected from the group consisting of $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro, and phenoxy, said phenoxy group being unsubstituted or substituted with one, two or three groups selected from the group consisting of $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxy-carbonyl-$C_{1-7}$-alkyl, $C_{1-7}$-alkyl-sulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro;

$R^3$ is hydrogen or halogen;

$R^4$ is selected from the group consisting of $—O—(CH_2)_m$-$NHR^5$, and $—O—(CO)—(CH_2)_n$-$NHR^6$, wherein m is selected from 1, 2 or 3, n is selected from 1 or 2, $R^5$ is selected from the group consisting of hydrogen, hydroxy-$C_{1-7}$-alkyl, amino-$C_{1-7}$-alkyl, $C_{1-7}$-alkyl-carbonyl, phenylcarbonyl, heteroarylcarbonyl, carboxyl, carboxyl-$C_{1-7}$-alkyl and $C_{1-7}$- alkoxy-carbonyl-amino-$C_{1-7}$-alkyl-carbonyl, and $R^6$ is selected from the group consisting of hydrogen, hydroxy-$C_{1-7}$-alkyl, amino-$C_{1-7}$-alkyl, $C_{1-7}$-alkyl-carbonyl, phenylcarbonyl, heteroarylcarbonyl, carboxyl, carboxyl-$C_{1-7}$-alkyl and $C_{1-7}$- alkoxy-carbonyl-amino-$C_{1-7}$-alkyl-carbonyl, or pharmaceutically acceptable salts thereof.

The invention is also concerned with processes for the manufacture of compounds of formula I.

The invention also relates to pharmaceutical compositions comprising a compound of formula I as described above and a pharmaceutically acceptable carrier and/or adjuvant.

A further aspect of the invention is the use of compounds of formula I as therapeutic active substances for the treatment of diseases that can be mediated with TLR agonists, in particular TLR7 and/or TLR8 agonists, more particularly TLR7 and TLR8 receptors. The invention thus relates to a method for the treatment of a disease that can be mediated with TLR agonists such as for example cancer and autoimmune or infectious diseases.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

The nomenclature used in this application is based on IUPAC systematic nomenclature, unless indicated otherwise.

The term “compound(s) of this invention” and “compound(s) of the present invention” refers to compounds of formula I and solvates or salts thereof (e.g., pharmaceutically acceptable salts).

The term “substituent” denotes an atom or a group of atoms replacing a hydrogen atom on the parent molecule.

The term “halogen” refers to fluoro, chloro, bromo and iodo, with fluoro, chloro and bromo being of particular interest. More particularly, halogen refers to fluoro and chloro.

The term “alkyl”, alone or in combination with other groups, refers to a branched or straight-chain monovalent saturated aliphatic hydrocarbon radical of one to twenty carbon atoms, particularly one to sixteen carbon atoms, more particularly one to ten carbon atoms. The term “$C_{1-10}$-alkyl” refers to a branched or straight-chain monovalent saturated aliphatic hydrocarbon radical of one to ten carbon atoms, such as e.g., methyl, ethyl, n-propyl, isopropyl, n-butyl, sec-butyl, tert-butyl, pentyl, 1,1,3,3-tetramethyl-butyl and the like. More particularly, the term “alkyl” also embraces lower alkyl groups as described below.

The term “lower alkyl” or “$C_{1-7}$-alkyl”, alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular methyl and ethyl.

The term “lower alkenyl” or “$C_{2-7}$-alkenyl” signifies a straight-chain or branched chain hydrocarbon residue comprising an olefinic bond and 2 to 7, in particular 3 to 6, more particularly 3 to 4 carbon atoms. Examples of alkenyl groups are ethenyl, 1-propenyl, 2-propenyl, isopropenyl, 1-butenyl, 2-butenyl, 3-butenyl and isobutenyl, in particular ethenyl.

The term “cycloalkyl” or “$C_{3-7}$-cycloalkyl” denotes a saturated monocyclic hydrocarbon group containing from 3 to 7 carbon atoms, such as cyclopropyl, cyclobutyl, cyclopentyl, cyclohexyl or cycloheptyl, more particularly cyclopropyl. In addition, the term "cycloalkyl" also embraces bicyclic hydrocarbon groups containing from 3 to 10 carbon atoms. Bicyclic means a cycloalkyl group consisting of two saturated carbocycles having one or more carbon atoms in common. Examples for bicyclic cycloalkyl are bicyclo [2.2.1]heptanyl or bicyclo[2.2.2]octanyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert-butoxy, in particular methoxy.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by a lower alkoxy group. Among the lower alkoxyalkyl groups of particular interest are methoxymethyl, 2-methoxyethyl and 2-ethoxyethyl, with 2-ethoxyethyl being of most particular interest.

The term hydroxy or hydroxyl means the group —OH.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the particular interesting lower hydroxyalkyl groups are hydroxymethyl or hydroxyethyl.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, most particularly fluoro. Among the lower halogenalkyl groups of particular interest are trifluoromethyl, difluoromethyl, trifluoroethyl, 2,2-difluoroethyl, fluoromethyl and chloromethyl, with trifluoromethyl being of more particular interest.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, particularly fluoro or chloro, most particularly fluoro. Among the lower halogenalkoxy groups of particular interest are trifluoromethoxy, difluoromethoxy, fluormethoxy and chloromethoxy, more particularly trifluoromethoxy.

The term "carboxyl" means the group —COOH.

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the lower carboxylalkyl groups or particular interest are carboxylmethyl ($—CH_2—COOH$) and carboxylethyl ($—CH_2—CH_2—COOH$).

The term "lower alkoxycarbonyl" or "$C_{1-7}$-alkoxycarbonyl" refers to the group —COOR, wherein R is lower alkyl and the term "lower alkyl" has the previously given significance. Lower alkoxycarbonyl groups of particular interest are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. A particular lower alkoxycarbonylalkyl group is $—CH_2—COOCH_3$.

The term "lower alkylcarbonyl" or "$C_{1-7}$-alkylcarbonyl" means the group —C(O)—R, wherein R is a lower alkyl group as defined above. A lower alkylcarbonyl group of particular interest is methylcarbonyl or acetyl.

The term "lower alkoxycarbonyl alkyl" or "$C_{1-7}$-alkoxycarbonyl-$C_{1-7}$-alkyl" refers to lower alkyl groups as defined above wherein at least one of the hydrogen atoms of the lower alkyl group is replaced by a lower alkoxycarbonyl group. Among the particular interesting lower alkoxycarbonyl-alkyl groups is $—(CH_2)_2—COOC_2H_5$.

The term "lower alkoxycarbonyl alkenyl" or "$C_{1-7}$-alkoxycarbonyl-$C_{2-7}$-alkenyl" refers to lower alkenyl groups as defined above wherein at least one of the hydrogen atoms of the lower alkenyl group is replaced by a lower alkoxycarbonyl group. Among the particular interesting lower alkoxycarbonyl-alkenyl groups is $—(CH_2)_2—COOC_2H_5$.

The term "lower alkylsulfonyl" or "$C_{1-7}$-alkylsulfonyl" means the group $—S(O)_2—R$, wherein R is a lower alkyl group as defined above. A lower alkylsulfonyl group of particular interest is methyl sulfonyl.

The term "lower alkylsulfonylalkyl" or "$C_{1-7}$-alkylsulfonyl-$C_{1-7}$-alkyl" means lower alkyl groups as defined above wherein one of the hydrogen atoms of the lower alkyl group is replaced by $C_{1-7}$-alkylsulfonyl. A particular lower alkylsulfonylalkyl group is $—CH_2—S(O)_2—CH_3$.

The term "lower hydroxyalkylsulfonyl" or "hydroxy-$C_{1-7}$-alkylsulfonyl" refers to lower alkylsulfonyl groups as defined above wherein at least one of the hydrogen atoms of the lower alkylsulfonyl group is replaced by a hydroxy group. Among the particular interesting lower hydroxyalkylsulfonyl groups are hydroxyethyl sulfonyl.

The term "lower alkoxyalkylsulfonyl" or "$C_{1-7}$-alkoxy-$C_{1-7}$-alkylsulfonyl" refers to lower alkylsulfonyl groups as defined above wherein at least one of the hydrogen atoms of the lower alkylsulfonyl group is replaced by a lower alkoxy group. Among the particular interesting lower alkoxyalkylsulfonyl groups are methoxyethylsulfonyl or ethoxyethylsulfonyl.

The term "lower alkoxycarbonyl alkyl sulfonyl" or "$C_{1-7}$-alkoxycarbonyl-$C_{1-7}$-alkylsulfonyl" refers to lower alkylsulfonyl groups as defined above wherein at least one of the hydrogen atoms of the lower alkylsulfonyl group is replaced by a lower alkoxycarbonyl group. Among the particular interesting lower alkoxycarbonyl-alkylsulfonyl groups is $—S(O)_2—(CH_2)_2—COOCH_3$.

The term "carboxylalkylsulfonyl" or "carboxyl-$C_{1-7}$-alkylsulfonyl" refers to lower alkylsulfonyl groups as defined above wherein at least one of the hydrogen atoms of the lower alkylsulfonyl group is replaced by a carboxyl group. Among the particular interesting lower carboxyl-alkylsulfonyl groups are $—S(O)_2—(CH_2)_3—COOH$ or $—S(O)_2—(CH_2)_4—COOH$.

The term "sulfamoyl" or "aminosulfonyl" means the group $—S(O)_2—NH_2$.

The term "lower alkylsulfamoyl" or "$C_{1-7}$-alkyl-sulfamoyl" defines the group $—S(O)_2—NH—R$, wherein R is lower alkyl and the term "lower alkyl" has the previously given meaning. An example of a lower alkylsulfamoyl group is methylsulfamoyl (methylaminosulfonyl).

The term "lower sulfamoylalkyl" or "sulfamoyl-$C_{1-7}$-alkyl" defines a lower alkyl group as defined above wherein one of the hydrogen atoms of the lower alkyl group is replaced by the group $—S(O)_2—NH_2$.

The term "lower alkylsulfamoylalkyl" or "$C_{1-7}$-alkyl-sulfamoylalkyl" defines a lower alkyl group as defined above wherein one of the hydrogen atoms of the lower alkyl group is replaced by the group $—S(O)_2—NH—R$, wherein R is lower alkyl and the term "lower alkyl" has the previously given meaning.

"Amino" refers to the group $—NH_2$. The term "$C_{1-7}$-alkylamino" means a group —NHR, wherein R is lower alkyl and the term "lower alkyl" has the previously given significance. The term "di-$C_{1-7}$-alkylamino" means a group —NRR', wherein R and R' are lower alkyl groups as defined above.

The term "lower aminoalkyl" or "amino-$C_{1-7}$-alkyl" refers to lower alkyl groups as defined above wherein at least one of the hydrogen atoms of the lower alkyl group is replaced by an amino group. Among the particular interesting lower aminoalkyl groups are aminomethyl or 2-aminoethyl.

The term "aminocarbonyl" refers to the group —CO—$NH_2$.

The term "lower aminoalkylcarbonyl" or "amino-$C_{1-7}$-alkyl-carbonyl" refers to the group —CO—R", wherein R" is a lower aminoalkyl group as defined herein before.

The term "lower aminocarbonyl alkyl" or "aminocarbonyl-$C_{1-7}$-alkyl" means lower alkyl groups as defined above wherein one of the hydrogen atoms of the lower alkyl group is replaced by aminocarbonyl. A lower aminoarbonylalkyl group of particular interest is —$CH_2$—$CONH_2$.

The term "lower alkylaminocarbonylalkyl" or "$C_{1-7}$-alkyl-aminocarbonyl-$C_{1-7}$-alkyl" refers to a lower alkyl group as defined above wherein one of the hydrogen atoms of the lower alkyl group is replaced by a group —CONH—R, wherein R is lower alkyl as defined herein before.

$C_{1-7}$-alkoxycarbonyl-amino-$C_{1-7}$-alkyl-carbonyl

The term "lower alkoxycarbonylaminoalkylcarbonyl" or "$C_{1-7}$-alkoxycarbonyl-amino-C $_{1-7}$-alkyl-carbonyl" refers to lower aminoalkylcarbonyl groups as defined above wherein at least one of the hydrogen atoms of the amino group is replaced by a lower alkoxycarbonyl group. Among the particular interesting lower alkoxycarbonyl-alkylsulfonyl groups is —CO—$(CH_2)_5$—NH—$COOC(CH_3)_3$.

The term "cyano" refers to the group —CN.

The term "nitro" refers to the group —$NO_2$.

The term "phenylcarbonyl" means the group —CO-Phe, wherein Phe stands for an optionally substituted phenyl group.

The term "heteroaryl" in general refers to an aromatic 5- or 6-membered ring which comprises one, two, three or four atoms selected from nitrogen, oxygen and/or sulfur, such as pyridyl, pyrazinyl, pyrimidinyl, 2,4-dioxo-1H-pyrimidinyl, pyridazinyl, 2-oxo-1,2-dihydropyridinyl, pyrrolyl, oxazolyl, oxadiazolyl, isoxazolyl, thiadiazolyl, tetrazolyl, pyrazolyl, imidazolyl, furanyl, thiazolyl, isothiazolyl, triazolyl, tetrazolyl, thienyl, azepinyl, diazepinyl. The term "heteroaryl" further refers to bicyclic aromatic groups comprising from 5 to 12 ring atoms, in which one or both rings can contain one, two or three atoms selected from nitrogen, oxygen or sulfur, such as quinolinyl, isoquinolinyl, cinnolinyl, quinazolinyl, pyrazolo[1,5-a]pyridyl, imidazo[1,2-a]pyridyl, quinoxalinyl, benzofuranyl, benzothienyl, benzothiazolyl, benzotriazolyl, indolyl and indazolyl. More particularly, "heteroaryl" refers to an aromatic 6-membered ring selected from the group consisting of pyridyl, pyrazinyl pyrimidinyl and pyridazinyl, more particularly pyridyl.

The term "oxo" means that a C-atom of the heteroaryl ring may be substituted by =O, thus meaning that the heteroaryl ring may contain one or more carbonyl (—CO—) groups.

The term "heteroarylcarbonyl" means the group —CO-Het, wherein Het is an optionally substituted heteroaryl group as defined above.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Pharmaceutically acceptable salts include both acid and base addition salts. The salts are for example acid addition salts of compounds of formula I with physiologically compatible mineral acids, such as hydrochloric acid, hydrobromic acid, nitric acid, carbonic acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxalic acid, lactic acid, trifluoroacetic acid, citric acid, fumaric acid, maleic acid, malonic acid, tartaric acid, benzoic acid, cinnamic acid, mandelic acid, embonic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium, zinc, copper, manganese and aluminium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, histidine, caffeine, procaine, hydrabamine, choline, betaine, ethylendiamine, glucosamine, methylglucamine, theobromine, piperazine, N-ethylpiperidine, piperidine and polyamine resins. The compound of formula I can also be present in the form of zwitterions. Pharmaceutically acceptable salts of compounds of formula I of particular interest are the sodium salts or salts with tertiary amines.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "half maximal effective concentration" ($EC_{50}$) denotes the plasma concentration of a particular compound required for obtaining 50% of the maximum of a particular effect in vivo.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgment of the attending medical or veterinary practitioner, and other factors.

In detail, the present invention relates to compounds of the formula

I

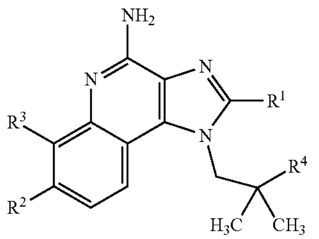

wherein $R^1$ is $C_{1-7}$-alkyl or $C_{1-7}$-alkoxy-$C_{1-7}$-alkyl;

$R^2$ is selected from the group consisting of hydrogen, halogen, hydroxyl, hydroxy-$C_{1-7}$-alkyl, alkoxy-$C_{1-7}$-alkyl, carboxyl, carboxyl-$C_{1-7}$-alkyl, carboxyl-$C_{2-7}$-alkenyl, aminocarbonyl-$C_{1-7}$-alkyl, aminocarbonyl-$C_{2-7}$-alkenyl, $C_{1-7}$-alkylamino-carbonyl-$C_{1-7}$-alkyl, $C_{1-7}$-alkylamino-carbonyl-$C_{2-7}$-alkenyl, $C_{1-7}$-alkoxy-carbonyl-$C_{1-7}$-alkyl, $C_{1-7}$-alkoxycarbonyl-$C_{2-7}$-alkenyl, $C_{1-7}$-alkyl-sulfonyl-$C_{1,7}$-alkyl, sulfamoyl-$C_{1-7}$-alkyl, $C_{1-7}$-alkyl-sulfamoyl-$C_{1-7}$-alkyl, phenyl, said phenyl being unsubstituted or substituted with one, two or three groups selected from the group consisting of $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro, and phenoxy, said phenoxy group being unsubstituted or substituted with one, two or three groups selected from the group consisting of $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxy-carbonyl-$C_{1-7}$-alkyl, $C_{1-7}$-alkyl-sulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro;

$R^3$ is hydrogen or halogen;

$R^4$ is selected from the group consisting of $—O—(CH_2)_m$-$NHR^5$, and $—O—(CO)—(CH_2)_n$-$NHR^6$, wherein m is selected from 1, 2 or 3, n is selected from 1 or 2, $R^5$ is selected from the group consisting of hydrogen, hydroxy-$C_{1-7}$-alkyl, amino-$C_{1-7}$-alkyl, $C_{1-7}$-alkyl-carbonyl, phenylcarbonyl, heteroarylcarbonyl, carboxyl, carboxyl-$C_{1-7}$-alkyl and $C_{1-7}$- alkoxy-carbonyl-amino-$C_{1-7}$-alkyl-carbonyl, and $R^6$ is selected from the group consisting of hydrogen, hydroxy-$C_{1-7}$-alkyl, amino-$C_{1-7}$-alkyl, $C_{1-7}$-alkyl-carbonyl, phenylcarbonyl, heteroarylcarbonyl, carboxyl, carboxyl-$C_{1-7}$-alkyl and $C_{1-7}$- alkoxy-carbonyl-amino-$C_{1-7}$-alkyl-carbonyl, or pharmaceutically acceptable salts thereof.

In a particular aspect, the present invention relates to compounds of the formula I-a

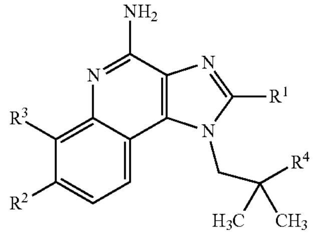

wherein $R^1$ is $C_{1-7}$-alkyl or $C_{1-7}$-alkoxy-$C_{1-7}$-alkyl;

$R^2$ is selected from the group consisting of hydrogen, hydroxyl, hydroxy-$C_{1-7}$-alkyl, $C_{1-7}$-alkoxy-$C_{1-7}$-alkyl, carboxyl, carboxyl-$C_{1-7}$-alkyl, aminocarbonyl-$C_{1-7}$-alkyl, $C_{1-7}$-alkylamino-carbonyl-$C_{1-7}$-alkyl, alkoxycarbonyl-$C_{1-7}$-alkyl, $C_{1-7}$-alkyl-sulfonyl-$C_{1-7}$-alkyl, sulfamoyl-$C_{1-7}$-alkyl, $C_{1-7}$-alkyl-sulfamoyl-$C_{1-7}$-alkyl, phenyl, said phenyl being unsubstituted or substituted with one, two or three groups selected from the group consisting of $C_{1-7}$-alkyl, $C_{3-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro, and phenoxy, said phenoxy group being unsubstituted or substituted with one, two or three groups selected from the group consisting of $C_{1-7}$-alkyl, $C_{3-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxy-carbonyl-$C_{1-7}$-alkyl, $C_{1-7}$-alkyl-sulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro;

$R^3$ is hydrogen or halogen;

$R^4$ is selected from the group consisting of $—O—(CH_2)_m$-$NHR^5$, and $—O—(CO)—(CH_2)_n$-$NHR^6$, wherein m is selected from 1, 2 or 3, n is selected from 1 or 2, $R^5$ is selected from the group consisting of hydrogen, hydroxy-$C_{1-7}$-alkyl, amino-$C_{1-7}$-alkyl, $C_{1-7}$-alkyl-carbonyl, phenylcarbonyl, heteroarylcarbonyl, carboxyl, and carboxyl-$C_{1-7}$-alkyl, and $R^6$ is selected from the group consisting of hydrogen, hydroxy-$C_{1-7}$-alkyl, amino-$C_{1-7}$-alkyl, $C_{1-7}$-alkyl-carbonyl, phenylcarbonyl, heteroarylcarbonyl, carboxyl, and carboxyl-$C_{1-7}$-alkyl, or pharmaceutically acceptable salts thereof.

In one aspect, the invention relates to compounds of formula I, wherein $R^1$ is $C_{1-7}$-alkoxy-$C_{1-7}$-alkyl. More particularly, $R^1$ is ethoxyethyl.

In another aspect, the invention refers to compounds of formula I, wherein $R^3$ is hydrogen.

In a further aspect, the invention relates to compounds of formula I, wherein $R^4$ is —O—$(CH_2)_m$-$NHR^5$ and wherein m is selected from 1, 2 or 3 and wherein $R^5$ is selected from the group consisting of hydrogen, hydroxy-$C_{1-7}$-alkyl, amino-$C_{1-7}$-alkyl, $C_{1-7}$-alkylcarbonyl, phenylcarbonyl, heteroarylcarbonyl, carboxyl, carboxyl-$C_{1-7}$-alkyl and $C_{1-7}$-alkoxycarbonyl-amino-$C_{1-7}$-alkyl-carbonyl. In particular, the invention refers to compounds of formula I, wherein $R^4$ is —O—$(CH_2)_m$-$NHR^5$ and wherein m is selected from 1, 2 or 3 and wherein $R^5$ is selected from the group consisting of hydrogen, hydroxy-$C_{1-7}$-alkyl, amino-$C_{1-7}$-alkyl, $C_{1-7}$-alkylcarbonyl, phenylcarbonyl, heteroarylcarbonyl, carboxyl, and carboxyl-$C_{1-7}$-alkyl.

In particular, the invention relates to compounds of formula I, wherein $R^4$ is —O—$(CH_2)_m$-$NHR^5$ and wherein m is 2 and $R^5$ is as defined herein before.

More particularly, the invention relates to compounds of formula I, wherein $R^4$ is —O—$(CH_2)_m$-$NHR^5$ and wherein m is 2 and wherein $R^5$ is selected from the group consisting of hydrogen, hydroxy-$C_{1-7}$-alkyl, $C_{1-7}$-alkylcarbonyl, heteroarylcarbonyl and $C_{1-7}$-alkoxycarbonyl-amino-$C_{1-7}$-alkyl-carbonyl, more particularly wherein $R^5$ is selected from the group consisting of hydrogen, hydroxy-$C_{1-7}$-alkyl, $C_{1-7}$-alkylcarbonyl and $C_{1-7}$-alkoxycarbonyl-amino-$C_{1-7}$-alkyl-carbonyl. Most particularly, the invention refers to a compound of formula I, wherein $R^4$ is —O—$(CH_2)_m$-$NHR^5$ and wherein m is 2 and $R^5$ is hydrogen.

The invention also relates to compounds of formula I, wherein $R^4$ is —O—$(CH_2)_m$-$NHR^5$ and wherein m is selected from 1, 2 or 3 and wherein $R^5$ is selected from the group consisting of hydrogen, hydroxy-$C_{1-7}$-alkyl, $C_{1-7}$-alkylcarbonyl and heteroarylcarbonyl. More particularly, the invention refers to compounds of formula I, wherein $R^4$ is —O—$(CH_2)_m$-$NHR^5$ and wherein m is selected from 1, 2 or 3 and wherein $R^5$ is hydrogen.

In another aspect, the invention refers to compounds of formula I, wherein $R^4$ is —O—(CO)—$(CH_2)_n$-$NHR^6$ and wherein n is selected from 1 or 2 and wherein $R^6$ is selected from the group consisting of hydrogen, hydroxy-$C_{1-7}$-alkyl, amino-$C_{1-7}$-alkyl, $C_{1-7}$-alkylcarbonyl, phenylcarbonyl, heteroarylcarbonyl, carboxyl, carboxyl-$C_{1-7}$-alkyl and $C_{1-7}$-alkoxycarbonyl-amino-$C_{1-7}$-alkyl-carbonyl.

In particular, the invention refers to compounds of formula I, wherein $R^4$ is —O—(CO)—$(CH_2)_n$-$NHR^6$ and wherein n is 1 or 2 and wherein $R^6$ is as defined herein before. More particularly, the invention relates to compounds of formula I, wherein $R^4$ is —O—(CO)—$(CH_2)_n$-$NHR^6$ and wherein n is 1 and $R^6$ is hydrogen.

In a further aspect, the invention also relates to compounds of formula I, wherein $R^4$ is —O—(CO)—$(CH_2)_n$-$NHR^6$ and wherein n is 1 or 2 and wherein $R^6$ is hydrogen.

The invention also relates to compounds of formula I, wherein $R^2$ is selected from the group consisting of hydrogen, halogen, hydroxyl, hydroxy-$C_{1-7}$-alkyl, alkoxy-$C_{1-7}$-alkyl, carboxyl, carboxyl-$C_{1-7}$-alkyl, carboxyl-$C_{2-7}$-alkenyl, aminocarbonyl-$C_{1-7}$-alkyl, aminocarbonyl-$C_{2-7}$-alkenyl, $C_{1-7}$-alkylamino-carbonyl-$C_{1-7}$-alkyl, $C_{1-7}$-alkylamino-carbonyl-$C_{2-7}$-alkenyl, $C_{1-7}$-alkoxycarbonyl-$C_{1-7}$-alkyl, $C_{1-7}$-alkoxycarbonyl-$C_{2-7}$-alkenyl, $C_{1-7}$-alkyl-sulfonyl-$C_{1-7}$-alkyl, sulfamoyl-$C_{1-7}$alkyl and $C_{1-7}$-alkyl-sulfamoyl-$C_{1-7}$-alkyl.

In another aspect, the invention relates to compounds of formula I, wherein $R^2$ is selected from the group consisting of hydrogen, halogen, $C_{1-7}$-alkoxycarbonyl-$C_{1-7}$-alkyl and $C_{1-7}$-alkoxycarbonyl-$C_{2-7}$-alkenyl.

In a particular aspect, the invention relates to compounds of formula I, wherein $R^2$ is hydrogen.

In another aspect, the invention relates to compounds of formula I, wherein $R^2$ is phenyl, said phenyl being unsubstituted or substituted with one, two or three groups selected from the group consisting of $C_{1-7}$-alkyl, $C_{3-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro, or to compounds of formula I, wherein $R^2$ is phenoxy, said phenoxy group being unsubstituted or substituted with one, two or three groups selected from the group consisting of $C_{1-7}$-alkyl, $C_{3-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkyl-sulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro.

Particular compounds of formula I according to the invention are the following:

1-(2-(2-aminoethoxy)-2-methylpropyl)-2-(ethoxymethyl)-1H-imidazo[4,5-c]quinolin-4-amine, 1-(4-amino-2-(ethoxymethyl)-1H-imidazo[4,5-c]quinolin-1-yl)-2-methylpropan-2-yl 2-aminoacetate, N-(2-(1-(4-amino-2-(ethoxymethyl)-1H-imidazo[4,5-c]quinolin-1-yl)-2-methylpropan-2-yloxy)ethyl)nicotinamide, N-(2-(1-(4-amino-2-(ethoxymethyl)-1H-imidazo[4,5-c]quinolin-1-yl)-2-methylpropan-2-yloxy)ethyl)acetamide, 3-(2-(1-(4-amino-2-(ethoxymethyl)-1H-imidazo[4,5-c]quinolin-1-yl)-2-methylpropan-2-yloxy)ethylamino)propan-1-ol, tert-butyl 6-(2-(1-(4-amino-2-(ethoxymethyl)-1H-imidazo[4,5-c]quinolin-1-yl)-2-methylpropan-2-yloxy)ethylamino)-6-oxohexylcarbamate, ethyl (E)-3-[4-amino-1-[2-(2-aminoethoxy)-2-methylpropyl]-2-(ethoxymethyl)-1H-imidazo[4,5-c]quinolin-7-yl]prop-2-enoate, ethyl 3-(4-amino-1-(2-(2-aminoethoxy)-2-methylpropyl)-2-(ethoxymethyl)-1H-imidazo[4,5-c] quinolin-7-yl)propanoate, ethyl 3-(4-amino-1-(2-(2-aminoacetoxy)-2-methylpropyl)-2-(ethoxymethyl)-1H-imidazo[4,5-c]quinolin-7-yl)propanoate, 1-(2-(2-aminoethoxy)-2-methylpropyl)-2-pentyl-1H-imidazo[4,5-c]quinolin-4-amine, 1-(2-(2-aminoethoxy)-2-methylpropyl)-7-bromo-2-(ethoxymethyl)-1H-imidazo[4,5-c]quinolin-4-amine, or pharmaceutically acceptable salts thereof.

Particularly, the invention relates to the following compounds of formula I:

1-(2-(2-aminoethoxy)-2-methylpropyl)-2-(ethoxymethyl)-1H-imidazo[4,5-c]quinolin-4-amine, 1-(4-amino-2-(ethoxymethyl)-1H-imidazo[4,5-c]quinolin-1-yl)-2-methylpropan-2-yl2-aminoacetate, ethyl 3-(4-amino-1-(2-(2-aminoethoxy)-2-methylpropyl)-2-(ethoxymethyl)-1H-imidazo[4,5-c]quinolin-7-yl)propanoate, or pharmaceutically acceptable salts thereof.

More particularly, the invention relates to a compound of formula I, which is 1-(2-(2-aminoethoxy)-2-methylpropyl)-2-(ethoxymethyl)-1H-imidazo[4,5-c]quinolin-4-amine, and pharmaceutically acceptable salts thereof.

More particularly, the invention relates to compounds of formula I selected from the group consisting of 1-(4-amino-2-(ethoxymethyl)-1H-imidazo[4,5-c]quinolin-1-yl)-2-methylpropan-2-yl 2-aminoacetate, ethyl 3-(4-amino-1-(2-(2-aminoethoxy)-2-methylpropyl)-2-(ethoxymethyl)-1H-imidazo[4,5-c]quinolin-7-yl)propanoate, and pharmaceutically acceptable salts thereof.

In particular, the invention refers to the following salts of compounds of formula I:

ethyl 3-(4-amino-1-(2-(2-aminoethoxy)-2-methylpropyl)-2-(ethoxymethyl)-1H-imidazo[4,5-c]quinolin-7-yl)propanoate hydrochloride, 1-(2-(2-aminoethoxy)-2-methylpropyl)-7-bromo-2-(ethoxymethyl)-1H-imidazo[4,5-c]quinolin-4-amine, or pharmaceutically acceptable salts thereof.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting an compound of the formula II

II

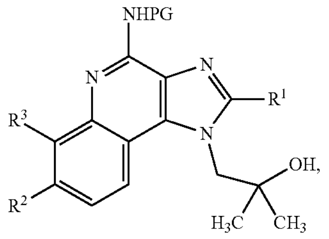

wherein $R^1$, $R^2$ and $R^3$ are as defined hereinbefore and PG is a protecting group, with a compound of the formula III

III

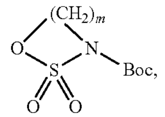

wherein m is as defined herein before, under basic conditions and removing the protecting groups PG and Boc under acidic conditions to obtain a compound of the formula I-a I-a

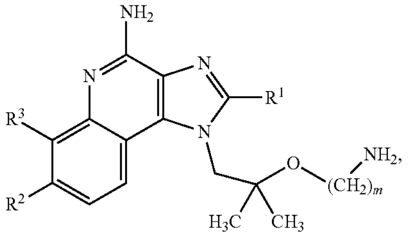

wherein $R^1$ to $R^3$ and m are as defined herein before, and optionally further coupling the compound of formula I-a with an alcohol or acid of the formula $R^5$—OH or and aldehyde of the formula $R^5$═O to obtain a compound of formula I-c I-c

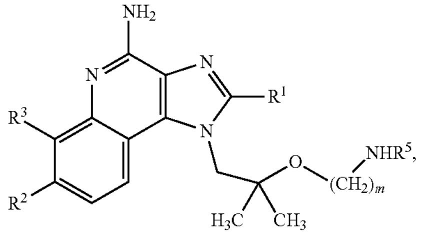

wherein $R^1$ to $R^3$, m and $R^5$ are as defined herein before, and, if desired, converting the compound obtained into a pharmaceutically acceptable salt, or b) reacting an compound of the formula II-a II-a

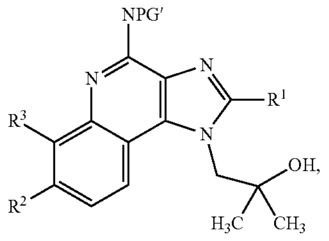

wherein $R^1$, $R^2$ and $R^3$ are as defined herein before and PG' is a protecting group, with a carboxylic acid of the formula IV

IV

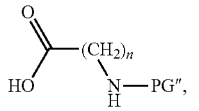

wherein n is defined as herein before and PG" is a protecting group, in the presence of a esterification agent and removing the protecting groups PG' and PG" with a mild reducing agent to obtain a compound of the formula I-b I-b

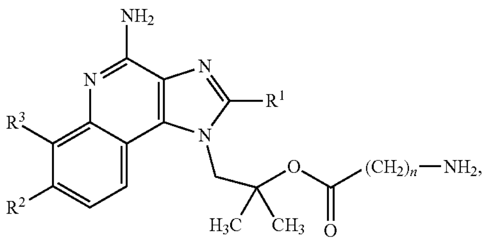

wherein $R^1$ to $R^3$ and n are as defined herein before, and optionally further coupling the compound of formula I-a with an alcohol or acid of the formula $R^6$-OH or and aldehyde of the formula $R^6{=}O$ to obtain a compound of formula I-d I-d

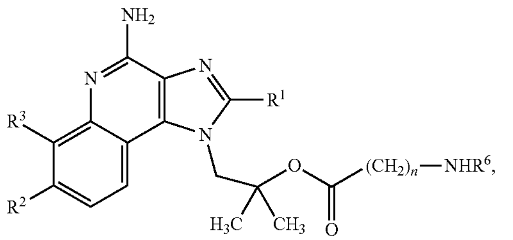

wherein $R^1$ to $R^3$, m and $R^6$ are as defined herein before, and, if desired, converting the compound obtained into a pharmaceutically acceptable salt.

In particular, a suitable protecting group PG is an amino-protecting group selected from trityl (TRT), or double protection by using an isoindoline-1,3-dione, bis-benzyl or bis-carboxybenzyl (bis-Z) protecting group.

"Under basic conditions" means the presence of a base such as sodium hydride or potassium tert-butylate. The reaction is carried out in a suitable solvent such as for example N,N-dimethylformamide (DMF), dimethylacetamide (DMA), dichloromethane or dioxane, at temperatures between 0° C. and room temperature.

"Removing the protecting groups PG and Boc under acidic conditions" means treating the protected compound with acids in a suitable solvent, for instance trifluoroacetic acid (TFA) in a solvent such as dichloromethane (DCM) can be employed.

Suitable protecting groups PG' and PG" are protecting groups that form a cyclic ring with the nitrogen atom of the amino group. In particular, PG' or PG" together with the nitrogen atom they are attached to, form an isoindoline-1,3-dione or signify a bis-benzyl or bis-carboxybenzyl protecting group.

An esterification agent is a compound that facilitates an esterification reaction. A particular esterification agent is N,N-diisopropyl-carbodiimide. The reaction is particularly carried out in an inert solvent, such as DCM.

"Removing the protecting groups PG' and PG" with a mild reducing agent" means in particular treating the protected compound with hydrazine/water in an inert solvent, such as THF.

The invention further relates to compounds of formula I as defined above obtainable according to a process as defined above.

The synthesis of the compounds with the general structure I can, for example, be accomplished according to the following schemes. Unless otherwise indicated, $R^1$ to $R^3$ and X are as defined above.

An access route to starting materials of formula AG is given in Scheme 1, and the route has been exemplified in WO 2013/033345 (Univ. of Minnesota).

Compounds AB can be obtained from suitably substituted orthoesters AA by condensation with 2-amino-propanedinitrile and 1-amino-2-methyl-propan-2-ol in an inert solvent, as for example THF in the presence of a base, like for example triethylamine. Suitable substituted orthoesters AA are commercially available, can be synthesized by a person skilled in the art or have been exemplified in the experimental part.

Compounds AC can be obtained from compounds AB by diazotization/iodination as known in the art; specifically by using diiodomethane as iodide source and isoamylnitrite as nitrite source in an inert solvent like chloroform at temperatures from 0° C. to the boiling temperature of the solvent, preferably at a temperature of 80° C.

Compounds of formula AC can be coupled with compounds of formula AD where M denotes a metal leaving group and R' denotes a hydrogen and/or a suitable protecting group, by methods known in the art, to give compounds of formula AE. Suitable metal leaving groups may be boronic acids, boronate esters, and trifluoroborates but also tin or zinc based leaving groups. In particular boronic acids or boronate esters can be used in Suzuki-Miyaura type couplings using a palladium catalyst, like $Pd(OAc)_2$ in the presence of triphenylphosphine, in an inert solvent, like DME, together with a suitable base, like sodium carbonate. The reaction temperature may range from room temperature to the boiling temperature of the solvent, with room temperature being a suitable choice in many cases.

If compounds AE are protected at the aniline amino group (one R' unequal H), deprotection to yield compounds of type AF can be done by methods known in the art, with acidic cleavage of the protecting group using TFA being a preferred choice.

Compounds of type AG can be obtained from compounds AF by thermal condensation (ring closure) in the presence of an acid catalyst. This can simply be achieved by heating compounds AF in an inert solvent, like dioxane, in the presence of an acid, like HCl, for an appropriate time, for example for 2 hours at 90° C.

Scheme 1

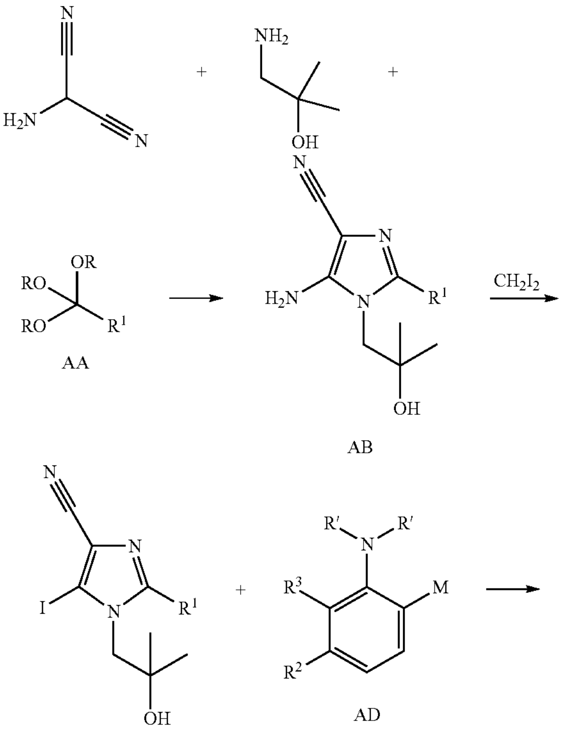

AA

AB

AC

AD

-continued

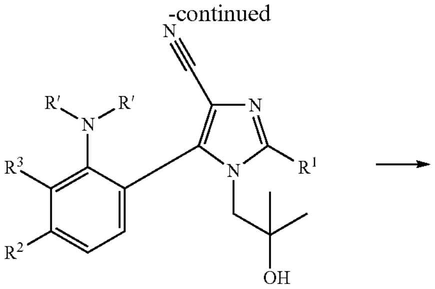

AE

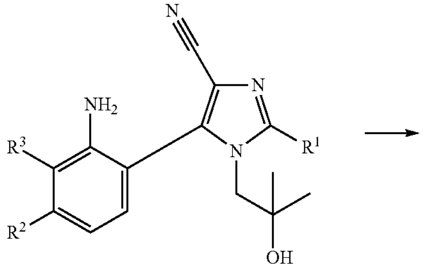

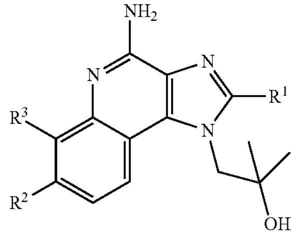

AG

Following the procedure according to scheme 2, compounds AG can be used as starting material for the synthesis of compounds I-a where $R^4$ is —O—$(CH_2)_m$-$NH_2$.

Compound BA can be obtained from AG by reaction with tritylchloride in the presence of a base in an inert solvent at elevated temperature with or without microwave irradiation. A suitable base-solvent combination is, for example, triethylamine or DIEA and acetonitrile, especially if the reaction is performed at elevated temperature in a microwave reactor.

Compounds of the general formula BC can be obtained from compounds of the general formula BA by reaction with the Boc-sulfamidate BB in a suitable solvent like DMF in the presence of a suitable base like sodium hydride of potassium tert-butylate. The reaction is advantageously performed at 0° C. to room temperature.

Compounds of the general formula I-a can be obtained from compounds of the general formula BC by removal of the protecting groups by treatment with acids in a suitable solvent. One such acid is TFA with or without additional DCM, used at room temperature.

Scheme 2

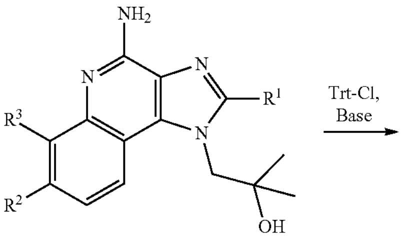

AG

-continued

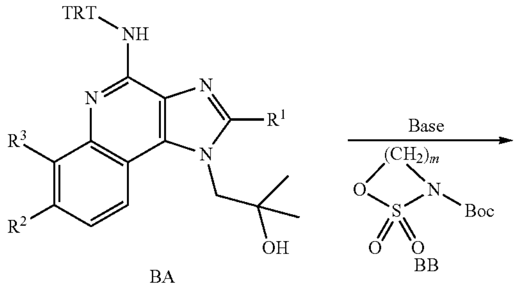

BA

BB

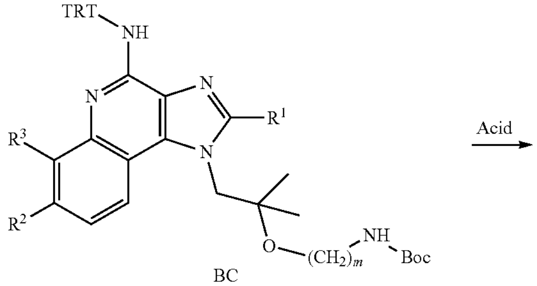

BC

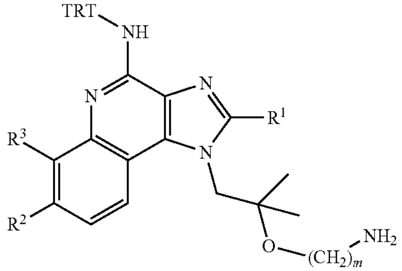

I-a

Following the procedure according to scheme 3, compound AG can be used as starting material for the synthesis of compounds I-b where $R^4$ is —O—(CO)—$(CH_2)_n$-$NH_2$.

Scheme 3

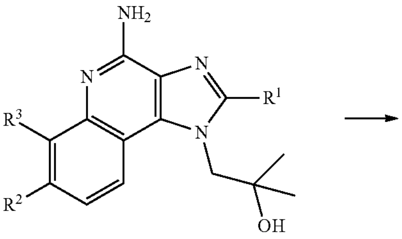

AG

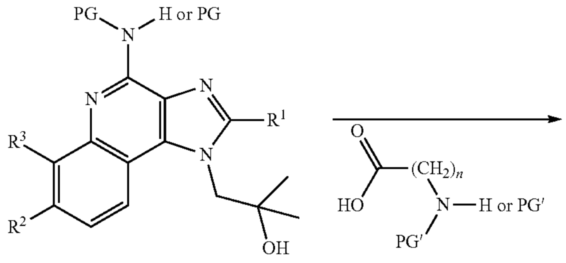

CA

CB

-continued

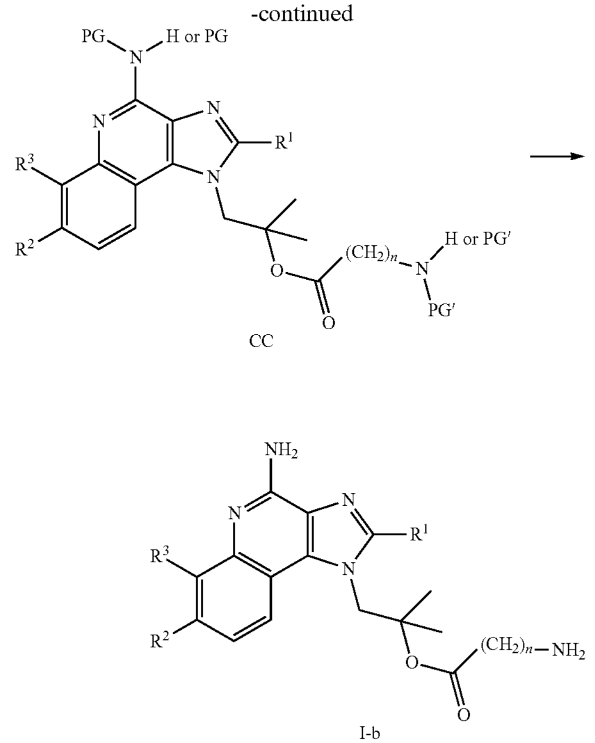

CC

I-b

Scheme 4

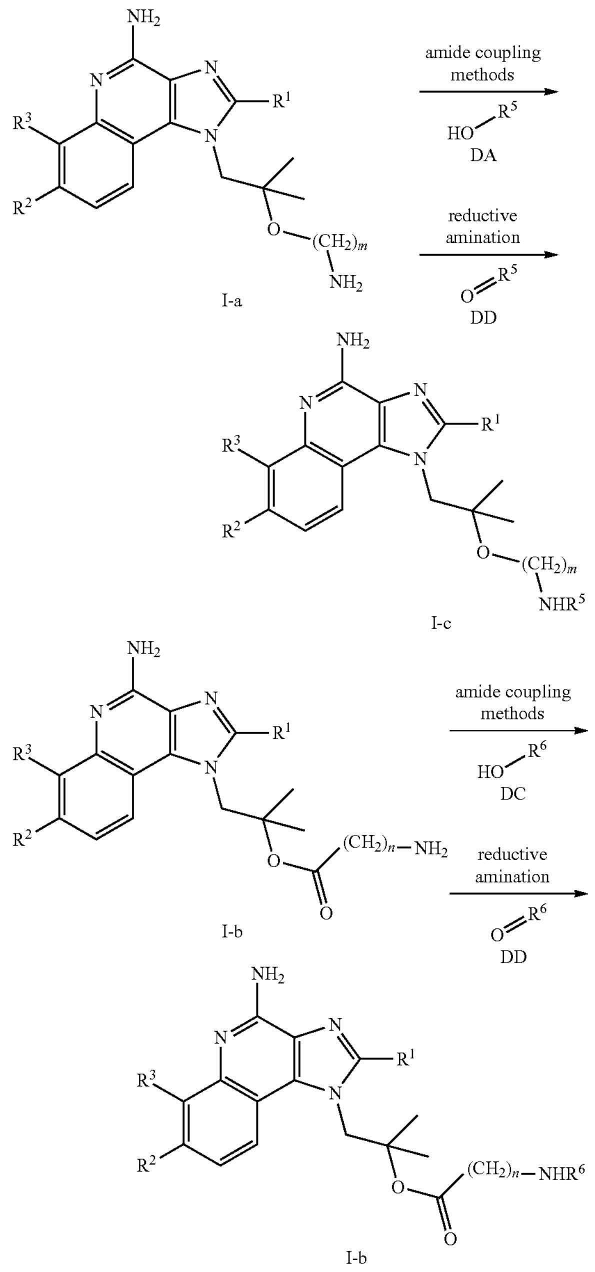

I-a

I-c

I-b

I-b

Compound CA can be obtained from AG by introduction of a suitable protecting group PG by methods known in the art. Such protecting groups may be for example the isoindoline-1,3-dione (phtalyl). Specifically, compound CA can be reacted with phtaloylchloride in the presence of a base, like 1,4-diazabicyclo[2,2,2]octane, in an inert, high boiling solvent such as toluene, at elevated temperatures to give a compound of type CA with isoindoline-1,3-dione as protecting group.

Compound CC can be obtained from compounds CB and CA by esterification using one of the many methods described in the art. Advantageously, such esterification can be accomplished by combining CB and CA in an inert solvent, like DCM, in the presence of N,N-diisopropyl-carbodiimide at elevated temperature. Suitable carboxylic acids CB are commercially available, can be prepared by procedures known in the art, or have been exemplified in the experimental part.

Compounds of the general formula I-b can be obtained from compounds of the general formula CC by removal of the protecting groups with methods known in the art. Specifically, the isoindoline-1,3-dione can be removed by treatment with hydrazine/water in an inert solvent, like THF, at room temperature.

Following the procedure according to scheme 4, compounds I-c and I-d can be obtained from I-a or I-b by methods known in the art, as for example amide couplings ($R^5$—OH or $R^6$—OH are acids) or reductive aminations ($R^5$═O or $R^6$═O are aldehydes) as explained in more detail in the experimental part.

If one of the starting materials, compounds of the formula AA, AD, AG, DA, DB, DC or DD, contains one or more functional groups which are not stable or are reactive under the reaction conditions of one or more reaction steps, appropriate protecting groups (PG) (as described e.g. in T. W. Greene et al., Protective Groups in Organic Chemistry, John Wiley and Sons Inc. New York 1999, 3rd edition) can be introduced before the critical step applying methods well known in the art. Such protecting groups can be removed at a later stage of the synthesis using standard methods known in the art.

If one or more compounds of the formula AA, AD, AG, DA, DB, DC or DD contain chiral centers, compounds of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

As described herein before, the compounds of formula I of the present invention can be used as medicaments for the treatment of diseases which are mediated by TLR agonists, in particular for the treatment of diseases which are mediated by TLR7 and/or TLR8 agonists, more particularly for the treatment of diseases which are mediated by TLR7 and TL8 agonists.

The compounds defined in the present invention are agonists of TLR7 and/or TLR8 receptors in cellular assays in vitro. More particularly, the compounds of the present invention are agonists of both TLR7 and TLR8 receptors. Accordingly, the compounds of the present invention are expected to be potentially useful agents in the treatment of diseases or medical conditions that may benefit from the activation of the immune system via TLR7 and/or TLR8 agonists, more particularly in the treatment of diseases or medical conditions that may benefit from the activation of the immune system via both TLR7 and TLR8 receptors. For example, the following diseases and conditions may be treatable with compounds of the present invention.

The compounds of formula I of the present invention are useful in oncology, i.e. they may be used in the treatment of common cancers including bladder cancer, head and neck cancer, prostate cancer, colorectal cancer, kidney cancer, breast cancer, lung cancer, ovarian cancer, cervical cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention and treatment of metastatic cancer and tumor recurrences, and paraneoplastic syndromes.

The compounds of formula I of the present invention are also useful in the treatment of autoimmune diseases. An "autoimmune disease" is a disease or disorder arising from and directed against an individual's own tissues or organs or a co-segregate or manifestation thereof or resulting condition therefrom. "Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). In a particular aspect, the autoimmune disease is associated with the skin, muscle tissue, and/or connective tissue.

Particular autoimmune diseases include autoimmune rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases, ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)), allergic conditions and responses, food allergies, drug allergies, insect allergies, rare allergic disorders such as mastocytosis, allergic reaction, eczema including allergic or atopic eczema, asthma such as bronchial asthma and auto-immune asthma, conditions involving infiltration of T cells and chronic inflammatory responses:

The compounds of formula I of the present invention are also useful in the treatment of infectious diseases. Thus, they may be useful in the treatment of viral diseases, in particular for diseases caused by infection with viruses selected from the group consisting of papilloma viruses, such as human papilloma virus (HPV) and those that cause genital warts, common warts and plantar warts, herpes simplex virus, molluscum contagiosum, hepatitis B virus (HBV), hepatitis C virus (HCV), Dengue virus, variola virus, human immunodeficiency virus (HIV), cytomegalovirus (CMV), varicella zoster virus (VZV), rhinovirus, enterovirus, adenovirus, coronavirus (e.g. SARS), influenza, mumps and parainfluenza.

They may also be useful in the treatment of bacterial diseases, in particular for diseases caused by infection with bacteria selected from the group consisting of mycobacterium such as *mycobacterium tuberculosis, mycobacterium avium* and *mycobacterium leprae*. The compounds of formula I of the present invention may further be useful in the treatment of other infectious diseases, such as chlamydia, fungal diseases, in particular fungal diseases selected from the group consisting of candidiasis, aspergillosis and cryptococcal meningitis, and parasitic diseases such as Pneumocystis carnii, pneumonia, cryptosporidiosis, histoplasmosis, toxoplasmosis, trypanosome infection and leishmaniasis.

Thus, the expression "diseases which are mediated by TLR agonists" means diseases which may be treated by activation of the immune system with TLR7 and /or TLR8 agonists such as cancer and infectious diseases. In particular, the expression "diseases which are mediated by TLR agonists" means cancers or autoimmune diseases or infectious diseases selected from the group consisting of viral diseases, bacterial diseases, fungal diseases and parasitic diseases.

In a particular aspect, the expression "which are mediated by TLR agonists" relates to cancer selected from the group consisting of bladder cancer, head and neck cancer, prostate cancer, colorectal cancer, kidney cancer, breast cancer, lung cancer, ovarian cancer, cervical cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma;

including the prevention and treatment of metastatic cancer and tumor recurrences, and paraneoplastic syndromes.

The invention also relates to pharmaceutical compositions comprising a compound of formula I as defined above and a pharmaceutically acceptable carrier and/or adjuvant. More specifically, the invention relates to pharmaceutical compositions useful for the treatment of diseases which are which are mediated by TLR agonists.

Further, the invention relates to compounds of formula I as defined above for use as therapeutically active substances, particularly as therapeutically active substances for the treatment of diseases which are which are mediated by TLR agonists. In particular, the invention relates to compounds of formula I for use in the treatment of cancers or autoimmune diseases or infectious diseases selected from the group consisting of viral diseases, bacterial diseases, fungal diseases and parasitic diseases.

In another aspect, the invention relates to a method for the treatment a of diseases which are mediated by TLR agonists, which method comprises administering a therapeutically active amount of a compound of formula I to a human being or animal. In particular, the invention relates to a method for the treatment of cancers and infectious diseases selected from the group consisting of viral diseases, bacterial diseases, fungal diseases and parasitic diseases.

The invention further relates to the use of compounds of formula I as defined above for the treatment of diseases which are mediated by TLR agonists.

In addition, the invention relates to the use of compounds of formula I as defined above for the preparation of medicaments for the treatment of diseases which are mediated by TLR agonists. In particular, the invention relates to the use of compounds of formula I as defined above for the preparation of medicaments for the treatment of cancers or autoimmune diseases or infectious diseases selected from the group consisting of viral diseases, bacterial diseases, fungal diseases and parasitic diseases.

In a further aspect, compounds of formula I can be in combination with one or more additional treatment modalities in a regimen for the treatment of cancer.

Combination therapy encompasses, in addition to the administration of a compound of the invention, the adjunctive use of one or more modalities that are effective in the treatment of cancer. Such modalities include, but are not limited to, chemotherapeutic agents, immunotherapeutics, anti-angiogenic agents, cytokines, hormones, antibodies, polynucleotides, radiation and photodynamic therapeutic agents. In a specific aspect, combination therapy can be used to prevent the recurrence of cancer, inhibit metastasis, or inhibit the growth and/or spread of cancer or metastasis. As used herein, "in combination with" means that the compound of formula I is administered as part of a treatment regimen that comprises one or more additional treatment modalities as mentioned above. The invention thus also relates to a method for the treatment of cancer, which method comprises administering a therapeutically active amount of a compound of formula I in combination with one or more other pharmaceutically active compounds to a human being or animal.

Compounds of formula I can be used alone or in combination with one or more additional treatment modalities in treating autoimmune diseases.

Combination therapy encompasses, in addition to the administration of a compound of the invention, the adjunctive use of one or more modalities that aid in the prevention or treatment of autoimmune diseases. Such modalities include, but are not limited to, chemotherapeutic agents, immunotherapeutics, anti-angiogenic agents, cytokines, hormones, antibodies, polynucleotides, radiation and photodynamic therapeutic agents. As used herein, "in combination with" means that the compound of formula I is administered as part of a treatment regimen that comprises one or more additional treatment modalities as mentioned above. The invention thus also relates to a method for the treatment of autoimmune diseases, which method comprises administering a therapeutically active amount of a compound of formula I in combination with one or more other pharmaceutically active compounds to a human being or animal.

In a further aspect, compounds of formula I can be used alone or in combination with one or more additional treatment modalities in treating infectious diseases.

Combination therapy encompasses, in addition to the administration of a compound of the invention, the adjunctive use of one or more modalities that aid in the prevention or treatment of infectious diseases. Such modalities include, but are not limited to, antiviral agents, antibiotics, and anti-fungal agents. As used herein, "in combination with" means that the compound of formula I is administered as part of a treatment regimen that comprises one or more additional treatment modalities as mentioned above. The invention thus also relates to a method for the treatment of infectious diseases, which method comprises administering a therapeutically active amount of a compound of formula I in combination with one or more other pharmaceutically active compounds to a human being or animal.

Pharmacological Test

The following tests were carried out in order to determine the activity of the compounds of formula I:

For TLR8 and TLR7 activity testing, HEK-Blue human TLR8 or TLR7 cells, respectively, (Invivogen, San Diego, Calif., USA) transfected with a SEAP reporter (secreted embryonic alkaline phosphatase) construct were used, in which the reporter expression is regulated by the NF-κB promoter upon stimulation for 24hr. The reporter activity was determined using Quanti Blue kit (Invivogen, San Diego, Calif., USA) at a wavelength of 640 nm.

$EC_{50}$ values were determined using Activity Base analysis (ID Business Solution, Limited).

The compounds according to formula I have an activity ($EC_{50}$ value) in the above assay for human TLR8 in the range of 0.01 nM to 11 μM, more particularly of 0.01 nM to 3 μM and in the above assay for human TLR7 in the range of 0.01 nM to 1 μM, in particular of 0.01 nM to 0.3 μM and more particularly of 0.01 nM to 0.1 μM.

For example, the following compounds showed the following EC50 values in the assay described above:

| Example | human TLR8 $EC_{50}$ [μM] | human TLR7 $EC_{50}$ [μM] |
|---|---|---|
| resiquimod | 9.6 | 0.76 |
| 1 | 0.58 | 0.06 |
| 2 | 0.08 | 0.05 |
| 3 | 35 | 0.223 |
| 4 | n.d. | 0.027 |
| 5 | 10.5 | 0.9 |
| 6 | 2.9 | 0.195 |
| 7 | 1.08 | 0.139 |
| 8 | 0.256 | 0.134 |
| 9 | 0.054 | 0.055 |

-continued

| Example | human TLR8 $EC_{50}$ [μM] | human TLR7 $EC_{50}$ [μM] |
|---|---|---|
| 10 | 2.7 | 0.152 |
| 11 | 2.9 | 0.13 |
| 1-(2-(2-Aminoethoxy)ethyl)-2-(ethoxymethyl)-1H-imidazo[4,5-c]quinolin-4-amine CAS Reg. No. 557787-49-2 (Example 69 in US 20030187016) | 49 | >100 |

Pharmaceutical Compositions

The compounds of formula I and their pharmaceutically acceptable salts can be used as medicaments, e.g., in the form of pharmaceutical preparations for enteral, parenteral or topical administration. The compounds of formula I and their pharmaceutically acceptable salts may be administered by systemic (e.g., parenteral) or local (e.g., topical or intralesional injection) administration. In some instances, the pharmaceutical formulation is topically, parenterally, orally, vaginally, intrauterine, intranasal, or by inhalation administered. As described herein, certain tissues may be preferred targets for the TLR agonist. Thus, administration of the TLR agonist to lymph nodes, spleen, bone marrow, blood, as well as tissue exposed to virus, are preferred sites of administration.

In one aspect, the pharmaceutical formulation comprising the compounds of formula I or its pharmaceutically acceptable salts is administered parenterally. Parenteral routes of administration include, but are not limited to, transdermal, transmucosal, nasopharyngeal, pulmonary and direct injection. Parenteral administration by injection may be by any parenteral injection route, including, but not limited to, intravenous (IV), including bolus and infusion (e.g., fast or slow), intraperitoneal (IP), intramuscular (IM), subcutaneous (SC) and intradermal (ID) routes. Transdermal and transmucosal administration may be accomplished by, for example, inclusion of a carrier (e.g., dimethylsulfoxide, DMSO), by application of electrical impulses (e.g., iontophoresis) or a combination thereof. A variety of devices are available for transdermal administration which may be used. Formulations of the compounds of formula I suitable for parenteral administration are generally formulated in USP water or water for injection and may further comprise pH buffers, salts bulking agents, preservatives, and other pharmaceutically acceptable excipients.

Transdermal administration is accomplished by application of a cream, rinse, gel, etc. capable of allowing the TLR agonist to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter. Administration via the transdermal and transmucosal routes may be continuous or pulsatile.

Pulmonary administration is accomplished by inhalation, and includes delivery routes such as intranasal, transbronchial and transalveolar routes. Formulations of compounds of formula I suitable for administration by inhalation including, but not limited to, liquid suspensions for forming aerosols as well as powder forms for dry powder inhalation delivery systems are provided. Devices suitable for administration by inhalation include, but are not limited to, atomizers, vaporizers, nebulizers, and dry powder inhalation delivery devices. Other methods of delivering to respiratory mucosa include delivery of liquid formulations, such as by nose drops. Administration by inhalation is preferably accomplished in discrete doses (e.g., via a metered dose inhaler), although delivery similar to an infusion may be accomplished through use of a nebulizer.

The compounds of formula I and pharmaceutically acceptable salts thereof may also be administered orally, e.g., in the form of tablets, coated tablets, dragées, hard and soft gelatine capsules.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples C1 to C3 illustrate typical compositions of the present invention, but serve merely as representative thereof.

Example C1

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example C2

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C3

Injection solutions can have the following composition:

| | |
|---|---|
| Compound of formula I | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

The following examples serve to illustrate the present invention in more detail. They are, however, not intended to limit its scope in any manner.

EXAMPLES

Example 1

1-(2-(2-Aminoethoxy)-2-methylpropyl)-2-(ethoxymethyl)-1H-imidazo[4,5-c]quinolin-4-amine a) 1-(2-(Ethoxymethyl)-4-(tritylamino)-1H-imidazo[4,5-c]quinolin-1-yl)-2-methylpropan-2-ol

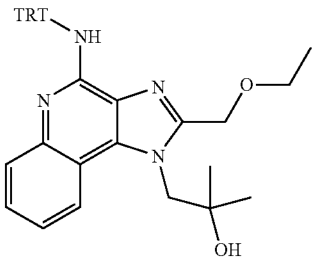

4-Amino-2-(ethoxymethyl)-α,α-dimethyl-1H-Imidazo[4,5-c]quinoline-1-ethanol (CAN 144875-48-9, 1.6 g, 5.09 mmol) was combined with acetonitrile (60 mL) to give a white suspension. Then triethylamine (1.77 mL, 12.7 mmol) and trityl chloride (1.7 g, 6.11 mmol) were added under Argon with stirring. The reaction mixture was irradiated in a microwave reactor at 100° C. for 30 minutes. Upon stirring the mixture the product precipitated and was isolated by filtration at 0° C., washed with cold acetonitrile and dried to yield the title compound (2.37 g, 83%) as white solid; MS (ESI): 557.5($MH^+$).

b) tert-Butyl 2-(1-(2-(ethoxymethyl)-4-(tritylamino)-1H-imidazo[4,5-c]quinolin-1-yl)-2-methylpropan-2-yloxy)ethylcarbamate

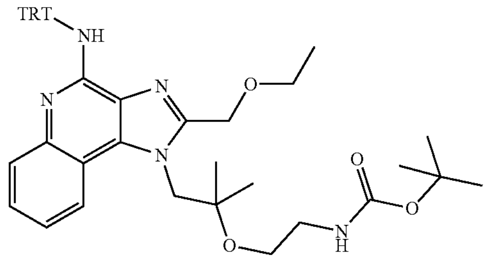

Sodium hydride dispersion in oil 60% (173 mg, 4.32 mmol) was combined with DMF (15 mL) to give a colorless suspension. The mixture was cooled to 0° C. with stirring, and at this temperature a solution of 1-(2-(ethoxymethyl)-4-(tritylamino)-1H-imidazo[4,5-c]quinolin-1-yl)-2-methylpropan-2-ol (1.85 g, 3.32 mmol) in DMF (15 mL) was added dropwise over a period of 10 min. Afterwards the reaction mixture was stirred for 1 hour at 0° C. and for 30 minutes at room temperature to give a yellow solution. To this solution was added at 0° C. 2,2-dioxide-1,2,3-oxathiazolidine-3-carboxylic acid-1,1-dimethylethyl ester (CAN 459817-82-4 , 964 mg, 4.32 mmol). The temperature was allowed to rise to room temperature and the mixture was stirred overnight. The mixture was poured into ice-water and extracted with ethyl acetate. Organic layers were washed with water/brine (2:1), combined, dried over $Na_2SO_4$, filtered and concentrated in vacuo. The residue was purified by flash chromatography (silica gel, 0 to 100% ethyl acetate in heptane) to give the title compound (1.47 g, 63%) as white foam; LC-MS (UV peak area, ESI) 98.7%, 700.3850 ($MH^+$).

c) 1-(2-(2-Aminoethoxy)-2-methylpropyl)-2-(ethoxymethyl)-1H-imidazo[4,5-c]quinolin-4-amine

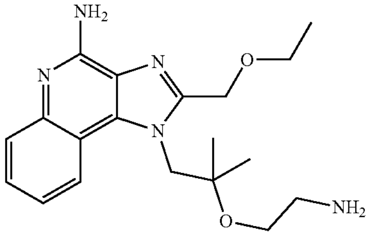 [SMILES: CCOCc1nc2c(N)nc3ccccc3c2n1CC(C)(C)OCCN]

tert-Butyl 2-(1-(2-(ethoxymethyl)-4-(tritylamino)-1H-imidazo[4,5-c]quinolin-1-yl)-2-methylpropan-2-yloxy)ethylcarbamate (1.45 g, 2.07 mmol) was combined with dichloromethane (DCM, 12 mL) to give a colorless solution. TFA (6.0 mL, 77.9 mmol) was added and the mixture was stirred for 3 hours at room temperature. The reaction mixture was cooled to 0° C., 2N sodium hydroxide solution (40 mL) was added, and the basic solution was extracted with dichloromethane. Organic layers were combined, dried over $Na_2SO_4$, filtered and concentrated in vacuo. The residue was purified by flash chromatography (silica gel, 0 to 10% methanol in DCM) to give the title compound (0.62 g, 83%) as white solid; LC-MS (UV peak area, ESI) 97.5%, 358.2238 ($MH^+$).

Example 2

1-(4-Amino-2-(ethoxymethyl)-1H-imidazo[4,5-c]quinolin-1-yl)-2-methylpropan-2-yl 2-aminoacetate a) 2-(2-(Ethoxymethyl)-1-(2-hydroxy-2-methylpropyl)-1H-imidazo[4,5-c]quinolin-4-yl)isoindoline-1,3-dione

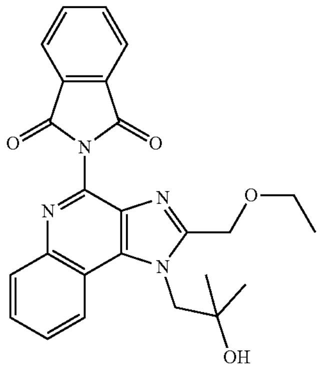 [SMILES: CCOCc1nc2c(N3C(=O)c4ccccc4C3=O)nc3ccccc3c2n1CC(C)(C)O]

4-Amino-2-(ethoxymethyl)-α,α-dimethyl-1H-imidazo[4,5-c]quinoline-1-ethanol (CAN 144875-48-9, 3.0 g, 9.54 mmol) was combined with toluene (21.0 mL) to give a white suspension. 1,4-Diazabicyclo[2.2.2]octane (3.21 g, 28.6 mmol) and phtaloyl chloride (1.65 mL, 11.5 mmol) were added with stirring and the reaction mixture was stirred at 110° C. for 4 hours. After cooling the mixture was diluted with ethyl acetate (300 mL) and washed with 1 N hydrochloric acid. Phases were separated and the water layer was extracted with ethyl acetate. The organic layers were combined, dried over $MgSO_4$, filtered and concentrated in vacuo. Upon stirring the residue with ethyl acetate (50 mL) the product precipitated, was filtered and dried in vacuo (1.9 g). The mother liquor was concentrated and yielded after flash chromatography (silica gel, 50 g, 0% to 100% EtOAc in heptane) another batch of product (0.59 g). In total 2.49 g (59%) of the title compound was isolated as white solid; LC-MS (UV peak area, ESI) 96%, 445.2 ($MH^+$).

b) 1-(4-(1,3-Dioxoisoindolin-2-yl)-2-(ethoxymethyl)-1H-imidazo[4,5-c]quinolin-1-yl)-2-methylpropan-2-yl 2-(1,3-dioxoisoindolin-2- yl)acetate

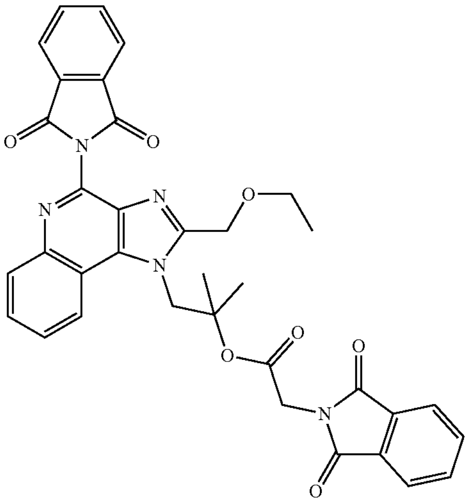 [SMILES: CCOCc1nc2c(N3C(=O)c4ccccc4C3=O)nc3ccccc3c2n1CC(C)(C)OC(=O)CN1C(=O)c2ccccc2C1=O]

2-(2-(Ethoxymethyl)-1-(2-hydroxy-2-methylpropyl)-1H-imidazo[4,5-c]quinolin-4-yl)isoindoline-1,3-dione (1600 mg, 3.6 mmol), 1,3-dihydro-1,3-dioxo-2H-isoindole-2-acetic acid (CAN 4702-13-0, 2.22 g, 10.8 mmol) and 4-(1-pyrrolidinyl)-pyridine (800 mg, 5.4 mmol) were combined with DCM (36 mL) to give a white suspension. N,N'-diisopropylcarbodiimide (1.68 mL, 10.8 mmol) and molecular sieves were added. The reaction mixture was heated to 50° C. and stirred for 2 hours and was, after cooling, filtered. The filtrate was diluted with DCM (150 mL) and washed with 1 N hydrochloric acid and water. Water phases were extracted with DCM, organic phases were combined, dried over $MgSO_4$, filtered and concentrated in vacuo. Diisopropylurea was removed after trituration with DCM/methanol by filtration, the filtrate was concentrated and the residue was purified by flash chromatography (silica gel, 0% to 100% ethyl acetate in heptane) to give a light yellow solid. Crystallization from DMSO yielded a first crop of product (1.95 g), and the mother liquor after concentration and preparative HPLC another 0.13 g of product. In total 2.08 g (91%) of the title compound was isolated as white solid; LC-MS (UV peak area, ESI) 95.9%, 632.2157 ($MH^+$).

c) 1-(4-Amino-2-(ethoxymethyl)-1H-imidazo[4,5-c]quinolin-1-yl)-2-methylpropan-2-yl 2-aminoacetate

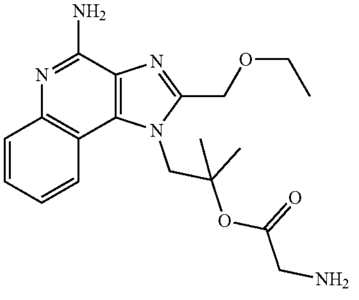 [SMILES: CCOCc1nc2c(N)nc3ccccc3c2n1CC(C)(C)OC(=O)CN]

1-(4-(1,3-Dioxoisoindolin-2-yl)-2-(ethoxymethyl)-1H-imidazo[4,5-c]quinolin-1-yl)-2-methylpropan-2-yl 2-(1,3-dioxoisoindolin-2-yl)acetate (300 mg, 475 μmol) was combined with THF (5 mL) to give a white suspension. To this suspension was added hydrazine in water (1000 μl, 11.2 mmol) and the solution was stirred for 0.75 hour at room temperature. The mixture was cooled to 0° C., 1N hydrochloric acid (30 mL) and DCM (50 mL) were added. The white precipitate a (phtalylhydrazide) was removed by filtration and the organic phase was discarded. The aqueous phase was lyophilized and the residue was taken up with acetonitrile (20 mL) and DIEA (pH 10). After evaporation of solvent, the residue was purified by preparative HPLC (Gemini NX 3u 50×4.6mm; acetonitrile/water/$Et_3N$) to give the title compound (111 mg, 63%) as amorphous white solid; LC-MS (UV peak area, ESI) 99%, 372.4 ($MH^+$).

Example 3

N-(2-(1-(4-Amino-2-(ethoxymethyl)-1H-imidazo[4,5-c]quinolin-1-yl)-2-methylpropan-2-yloxy)ethyl)nicotinamide

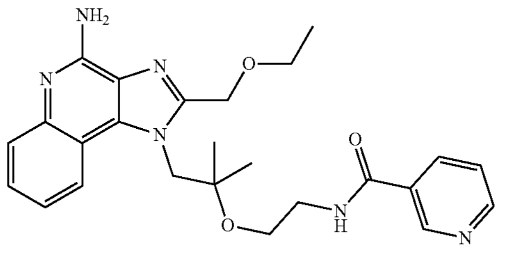 [SMILES: CCOCc1nc2c(N)nc3ccccc3c2n1CC(C)(C)OCCNC(=O)c1cccnc1]

Nicotinic acid (11.4 mg, 92.3 μmol) was combined with DMF (1.0 mL) to give a colorless solution. To this solution was added TBTU (29.6 mg, 92.3 μmol), and DIEA (54.2 mg, 71.8 μl) were added. Finally 1-(2-(2-aminoethoxy)-2-methylpropyl)-2-(ethoxymethyl)-1H-imidazo[4,5-c]quinolin-4-amine (30 mg, 83.9 μmol) was added and the reaction mixture was stirred for 1 hour at room temperature. Volatiles were removed in high vacuum at 40° C. The residue was dissolve in a mixture of ethyl acetate (5 mL) and methanol (0.5 mL). 1N sodium hydroxide solution (1.5 mL) was added and after a few minutes stirring the layers were separated. The aqueous layer was extracted with ethyl acetate. The organic phases were combined dried over $Na_2SO_4$, filtered and concentrated in vacuo. The residue was purified by flash chromatography (silica gel-NH2, 0% to 10% methanol in DCM) to give the title product (33 mg, 85%) as white foam; LC-MS (UV peak area, ESI) 88%, 463.2459 ($MH^+$).

Example 4

N-(2-(1-(4-Amino-2-(ethoxymethyl)-1H-imidazo[4,5-c]quinolin-1-yl)-2-methylpropan-2-yloxy)ethyl)acetamide

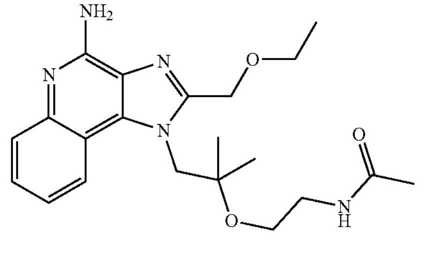 [SMILES: CCOCc1nc2c(N)nc3ccccc3c2n1CC(C)(C)OCCNC(C)=O]

1-(2-(2-Aminoethoxy)-2-methylpropyl)-2-(ethoxymethyl)-1H-imidazo[4,5-c]quinolin-4-amine (32 mg, 89.5 μmol) was combined with DCM (1.0 mL) to give a colorless solution. To this solution was added triethylamine (25.0 μL, 179 μmol) and acetyl chloride (7.00 μL , 98.5 μmol) and the reaction mixture was stirred 18 hours at room temperature. After concentrating the mixture in vacuo the residue was purified by flash chromatography (silica gel-$NH_2$, 0% to 10% methanol in DCM) to give the title compound (19 mg, 53%) as white foam; LC-MS (UV peak area, ESI) 97%, 400.2348 ($MH^+$).

Example 5

3-(2-(1-(4-Amino-2-(ethoxymethyl)-1H-imidazo[4,5-c]quinolin-1-yl)-2-methylpropan-2-yloxy)ethylamino)propan-1-ol a) 2-(Ethoxymethyl)-1-[2-methyl-2-[2-(3-trityloxypropylamino)ethoxy]propyl]-imidazo[4,5-c]quinolin-4-amine

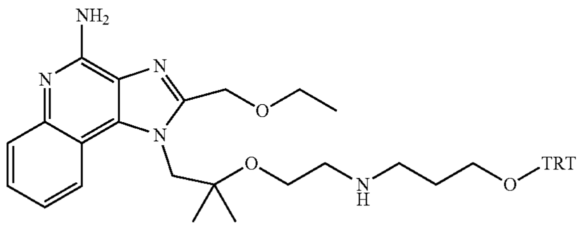

1-(2-(2-Aminoethoxy)-2-methylpropyl)-2-(ethoxymethyl)-1H-imidazo[4,5-c]quinolin-4-amine (50 mg, 140 μmol) and 3-(triphenylmethoxy)-propanal (CAN 67057-68-5; 44.3 mg, 140 μmol) were combined with ethanol (500 μL) to give a light yellow suspension. The mixture was stirred for 2 hours at room temperature. Afterwards sodium borohydride (5.82 mg, 154 μmol) was added and stirring at room temperature continued overnight. The mixture was stirred with water (2 mL) and ethyl acetate (5 mL), dried by passage through a ChemElut® cartridge and concentrated in vacuo. The crude material was purified by flash chromatography (silica gel-NH2, 0% to 100% ethyl acetate in heptane) followed by another flash chromatography (silica gel, 0 to 10% methanol in ethyl acetate) to give the title compound (10 mg, 11%) as yellowish gum; LC-MS (UV peak area, ESI) 89%, 658.5 ($MH^+$).

b) 3-(2-(1-(4-Amino-2-(ethoxymethyl)-1H-imidazo[4,5-c]quinolin-1-yl)-2-methylpropan-2-yloxy)ethylamino)propan-1-ol

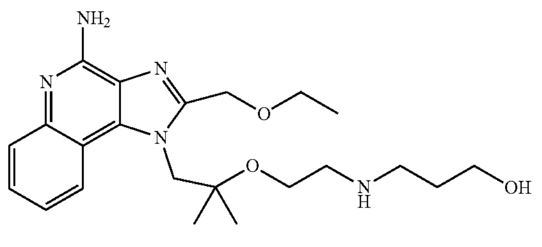 [SMILES: CCOCc1nc2c(N)nc3ccccc3c2n1CC(C)(C)OCCNCCCO]

2-(Ethoxymethyl)-1-[2-methyl-2-[2-(3-trityloxypropylamino)ethoxy]propyl]-imidazo[4,5-c]quinolin-4-amine (10 mg, 15.2 μmol) was combined with DCM (1 mL) to give a colorless solution. TFA (100 μl, 1.3 mmol) was added and the reaction mixture was stirred at room temperature for 5 hours. The mixture was concentrated in vacuo and the residue was purified by flash chromatography (silica gel-NH2, 0% to 30% methanol in ethyl acetate) to give the title compound (2.3 mg, 36%) as colorless gum; LC-MS (UV peak area, ESI) 95.6%, 416.2661 ($MH^+$).

Example 6 tert-Butyl 6-(2-(1-(4-amino-2-(ethoxymethyl)-1H-imidazo[4,5-c]quinolin-1-yl)-2-methylpropan-2-yloxy)ethylamino)-6-oxohexylcarbamate

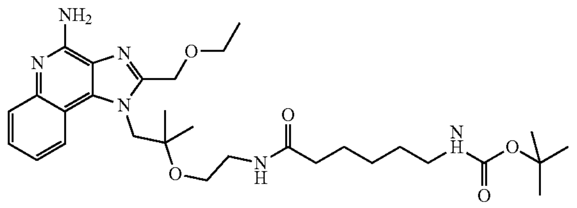 [SMILES: CCOCc1nc2c(N)nc3ccccc3c2n1CC(C)(C)OCCNC(=O)CCCCCNC(=O)OC(C)(C)C]

6-(tert-Butoxycarbonylamino)hexanoic acid (197 mg, 850 μmol) was combined with DMF (10.9 mL) to give a colorless solution. O-(Benzotriazol-1-yl)-N,N,N',N'-tetramethyluronium tetrafluoroborate (TBTU, 300 mg, 936 μmol) and N,N-diisopropylethylamine (DIEA, 728 μl, 4.25 mmol) were added with stirring in an inert atmosphere. Then 1-(2-(2-aminoethoxy)-2-methylpropyl)-2-(ethoxymethyl)-1H-imidazo[4,5-c]quinolin-4-amine (Example 1c, 304 mg, 850 μmol) was added and the mixture was stirred for 2 hours at room temperature. The mixture was concentrated in vacuo, dissolved in ethyl acetate (5 mL), stirred for 1 min with cold sodium hydroxide solution (1 N) and dried by passing through ChemElut® (10 g). The organic phase was concentrated in vacuo again and the residue was purified by flash chromatography (silica gel, 10% methanol in dichloromethane) to give the title compound (0.135 g, 23%) as light brown oil; LC-MS (UV peak area, ESI) 83%, 571.5 ($MH^+$).

Example 7

(E)-Ethyl 3 -(4-amino-1-(2-(2-aminoethoxy)-2-methylpropyl)-2-(ethoxymethyl)-1H-imidazo[4,5-c]quinolin-7-yl)acrylate a) 5-Amino-2-(ethoxymethyl)-1-(2-hydroxy-2-methylpropyl)-1H-imidazole-4-carbonitrile

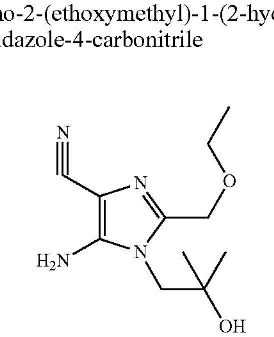

Triethylamine (5.28 ml, 37.9 mmol) was added with stirring to a suspension of 2-aminomalononitrile 4-methylbenzenesulfonate (8 g, 31.6 mmol) in THF (120 ml) to give a light brown solution. 1,1,1,2-Tetraethoxyethane (7.82 g, 37.9 mmol) was added and the reaction mixture was stirred under argon at reflux temperature. After 4 h an additional amount of 2.3 g 1,1,1,2-tetraethoxyethane was added and the mixture heated for another 2 h. The mixture was allowed to cool to room temperature, triethylamine (5.28 ml, 37.9 mmol) and 1-amino-2-methylpropan-2-ol (3.63 ml, 37.9 mmol) were added and the reaction was stirred overnight. The mixture was concentrated in vacuo, and the residue was partitioned between ethyl acetate (200 mL, 2×150 mL) and sodium bicarbonate solution (2 M, 100 mL). The organic phases were combined, dried over $MgSO_4$, concentrated in vacuo and purified by flash chromatography (silica gel, 0% to 100% ethyl acetate in heptane) to give the title compound after a crystallization step from heptane (4.47 g, 59%) as white crystalline solid; LC-MS (UV peak area, ESI) 100%, 239.1514 (MH+).

b) 2-(Ethoxymethyl)-1-(2-hydroxy-2-methylpropyl)-5-iodo-1H-imidazole-4-carbonitrile

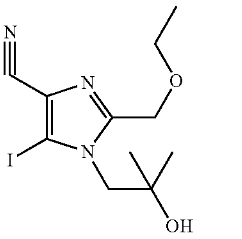 [SMILES: CCOCc1nc(C#N)c(I)n1CC(C)(C)O]

Diiodomethane (14.5 ml, 180 mmol) was added under argon with stirring to a suspension of 5-amino-2-(ethoxymethyl)-1-(2-hydroxy-2-methylpropyl)-1H-imidazole-4-carbonitrile (4.36 g, 18.3 mmol) in chloroform (170 mL). The reaction mixture was heated to 80° C., a solution of isoamyl nitrite (9.86 ml, 73.2 mmol) in chloroform (30 mL) was added with a syringe pump over a period of 40 min and the mixture was stirred for another 30 min at 80° C. After cooling to room temperature the mixture was concentrated in vacuo and purified by flash chromatography (silica gel, 20% to 50% ethyl acetate in heptane) to give the title compound (3.66 g, 57%) as brown oil; LC-MS (UV peak area, ESI) 90%, 350.0374 ($MH^+$).

c) Methyl 3-amino-4-[5-cyano-2-(ethoxymethyl)-3-(2-hydroxy-2-methylpropyl)-1H-imidazol-4-yl]benzoate

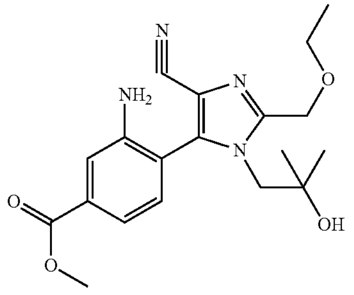 [SMILES: CCOCc1nc(C#N)c(-c2ccc(C(=O)OC)cc2N)n1CC(C)(C)O]

In an inert atmosphere 2-(ethoxymethyl)-1-(2-hydroxy-2-methylpropyl)-5-iodo-1H-imidazole-4-carbonitrile (3.66 g, 10.5 mmol) was combined with dimethoxyethane (43 mL) to give a light brown solution. To this solution were added $Pd(OAc)_2$ (118 mg, 524 μmol), triphenylphosphine (275 mg, 1.05 mmol) and methyl 3-amino-4-(4,4,5,5-tetramethyl-1,3,2-dioxaborolan-2-yl)benzoate (4.36 g, 15.7 mmol) with stirring. Finally $Na_2CO_3$ (2 M, 15.7 mL, 31.4 mmol) was added. The reaction mixture was heated to 100° C. and stirred for 1 hour. After cooling to room temperature the mixture was partitioned between ethyl acetate (70 mL, 2×50 mL) and water (70 mL). The organic phases were combined, dried over $MgSO_4$, concentrated in vacuo and purified by flash chromatography (silica gel, 0% to 100% ethyl acetate in heptane) to give the title compound (2.79 g, 71%) as light brown foam that was used in the next step without further purification.

d) Methyl 4-amino-2-(ethoxymethyl)-1-(2-hydroxy-2-methylpropyl)-1H-imidazo[4,5-c]quinoline-7-carboxylate

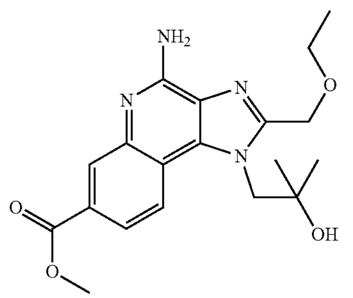 [SMILES: CCOCc1nc2c(N)nc3cc(C(=O)OC)ccc3c2n1CC(C)(C)O]

Methyl 3-amino-4-(4-cyano-2-(ethoxymethyl)-1-(2-hydroxy-2-methylpropyl)-1H-imidazol-5-yl)benzoate (2.79 g, 7.49 mmol) was combined with a solution of HCl in dioxane (4M, 56.2 mL, 225 mmol) to give an orange solution. The reaction mixture was heated to 90° C. under argon with stirring. After 1 h at 90° C. the mixture was cooled to room temperature and concentrated in vacuo to obtain a beige solid. The solid was dissolved in ethyl acetate (500 mL) washed with a mixture of water (100 mL) and saturated sodium bicarbonate solution (250 mL). The water phase was extracted with ethyl acetate (2×250 mL), organic phases were combined, dried with $MgSO_4$ and concentrated in vacuo to obtain a yellow solid (3.05 g). The solid material was re-crystallized from ethyl acetate/heptane to give the title compound (2.4 g, 86%) as light yellow solid; LC-MS (UV peak area, ESI) 99%, 373.1884 (MH+).

e) Methyl 2-(ethoxymethyl)-1-(2-hydroxy-2-methylpropyl)-4-(tritylamino)-1H-imidazo[4,5-c]quinoline-7-carboxylate

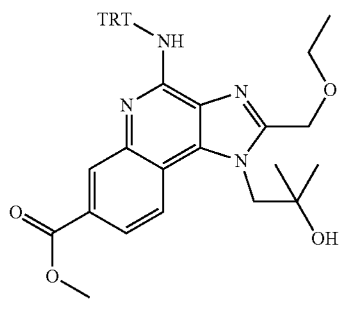

The title compound was synthesized in analogy to Example 1a, using methyl 4-amino-2-(ethoxymethyl)-1-(2-hydroxy-2-methylpropyl)-1H-imidazo[4,5-c]quinoline-7-carboxylate as starting material and isolated (0.77 g, 96%) as light brown solid; LC-MS (UV peak area, ESI) 96%, 615.4 ($MH^+$).

f) 2-(Ethoxymethyl)-1-(2-hydroxy-2-methylpropyl)-4-(tritylamino)-1H-imidazo[4,5-c]quinoline-7-carboxylic acid

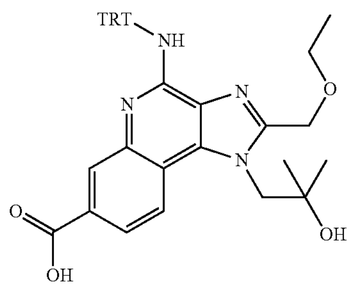

Sodium hydroxide solution (1 N, 3.51 ml) was added to methyl 2-(ethoxymethyl)-1-(2-hydroxy-2-methylpropyl)-4-(tritylamino)-1H-imidazo[4,5-c]quinoline-7-carboxylate (540 mg, 878 μmol) dissolved in THF (6.21 mL) and methanol (621 μL). The reaction mixture was stirred for 120 hours at room temperature and concentrated in vacuo. The residue was partitioned between ethyl acetate (30 mL) and cold 1M HCl solution (5 mL). The aqueous layer was extracted with ethyl acetate (2×50 mL). Organic layers were washed with water (20 mL) and brine (20 mL), combined, dried with $MgSO_4$, and concentrated in vacuo to obtain the title compound (0.499 g, 94%) as white solid; LC-MS (UV peak area, ESI) 99%, 601.3 ($MH^+$).

g) 2-(Ethoxymethyl)-1-(2-hydroxy-2-methylpropyl)-N-methoxy-N-methyl-4-(tritylamino)-1H-imidazo[4,5-c]quinoline-7-carboxamide

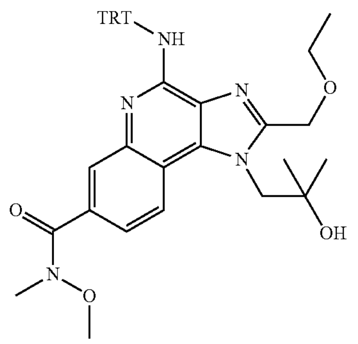

To a solution of 2-(ethoxymethyl)-1-(2-hydroxy-2-methylpropyl)-4-(tritylamino)-1H-imidazo[4,5-c]quinoline-7-carboxylic acid (484 mg, 741 μmol) in DMF (5.19 mL) in an inert atmosphere was added TBTU (357 mg, 1.11 mmol), DIEA (388 μL, 2.22 mmol) and N,O-dimethylhydroxylamine hydrochloride (108 mg, 1.11 mmol) with stirring. The reaction mixture was stirred for 1 h at room temperature and afterwards the mixture was concentrated in vacuo. The residue was partitioned between ethyl acetate (40 mL, 2×20 mL) and water (40 mL). The organic phases were washed with water (2×20 mL), combined, dried over $MgSO_4$, concentrated in vacuo and purified by flash chromatography (silica gel, 50% to 100% ethyl acetate in heptane) to give the title compound (0.53 g, quant.) as white foam; LC-MS (UV peak area, ESI) 92%, 644.4 ($MH^+$).

h) 2-(Ethoxymethyl)-1-(2-hydroxy-2-methylpropyl)-4-(tritylamino)-1H-imidazo[4,5-c]quinoline-7-carbaldehyde

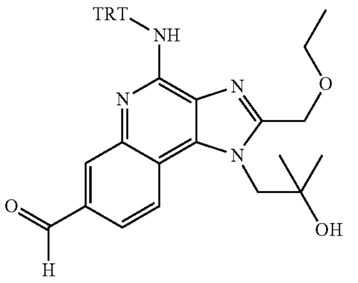

To a solution of 2-(ethoxymethyl)-1-(2-hydroxy-2-methylpropyl)-N-methoxy-N-methyl-4-(tritylamino)-1H-imidazo[4,5-c]quinoline-7-carboxamide (520 mg, 808 μmol) in THF (7 mL) in an inert atmosphere was added with stirring at 0° C. a solution of lithium aluminum hydride in THF (1 M, 404 μl, 404 μmol). The mixture was stirred 1 h at 0° C., saturated ammonium chloride solution (10 mL) was added slowly and finally water (20 mL) and ethyl acetate (30 mL) were added. The phases were separated, the water layer was extracted with ethyl acetate (30 mL), and the organic phases were washed with water (20 mL), combined, dried with $MgSO_4$, and concentrated in vacuo to give the title compound (0.49 g, quant.) as white foam (LC-MS (UV peak area, ESI) 83%, 585.4 ($MH^+$)) that was used in the next step without further purification.

i) Ethyl (E)-3-[2-(ethoxymethyl)-1-(2-hydroxy-2-methylpropyl)-4-(tritylamino)-1H-imidazo[4,5-c]quinolin-7-yl]prop-2-enoate

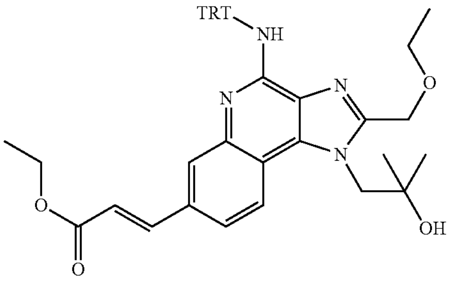

(Carbethoxymethylene)triphenylphosphorane (422 mg, 1.21 mmol) was added to a solution of 2-(ethoxymethyl)-1-(2-hydroxy-2-methylpropyl)-4-(tritylamino)-1H-imidazo[4,5-c]quinoline-7-carbaldehyde (472 mg, 808 μmol) in dichloromethane (8 mL) under argon. The reaction mixture was stirred for 20 h at room temperature and concentrated in vacuo. Crystallization from dichloromethane and diethyl ether afforded the title compound (0.399 g, 75%) as white solid, LC-MS (UV peak area, ESI) 89%, 655.4 ($MH^+$).

j) Ethyl (E)-3-[1-[2-[2-(tert-butoxycarbonylamino)ethoxy]-2-methylpropyl]-2-(ethoxymethyl)-4-(tritylamino)-1H-imidazo[4,5-c]quinolin-7-yl]prop-2-enoate

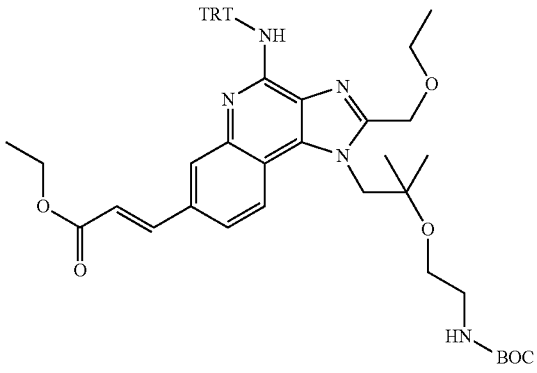

The title compound was synthesized in analogy to Example 1b, using ethyl (E)-3-[2-(ethoxymethyl)-1-(2-hydroxy-2-methylpropyl)-4-(tritylamino)-1H-imidazo[4,5-c]quinolin-7-yl]prop-2-enoate as starting material and isolated (0.28 g, 42%) as white solid; LC-MS (UV peak area, ESI) 76%, 798.6 ($MH^+$).

k) Ethyl (E)-3-[4-amino-1-[2-(2-aminoethoxy)-2-methylpropyl]-2-(ethoxymethyl)imidazo[4,5-c]quinolin-7-yl]prop-2-enoate

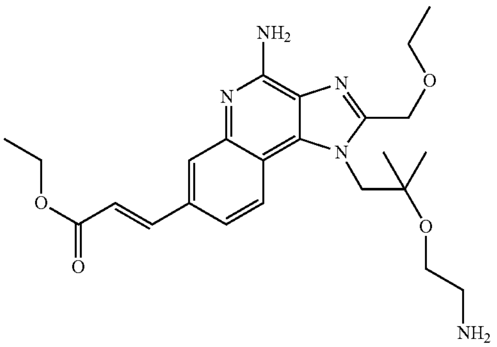 [SMILES: CCOCc1nc2c(N)nc3cc(/C=C/C(=O)OCC)ccc3c2n1CC(C)(C)OCCN]

The title compound was synthesized in analogy to Example 1c, using ethyl (E)-3-[1-[2-[2-(tert-butoxycarbonylamino)ethoxy]-2-methylpropyl]-2-(ethoxymethyl)-4-(tritylamino)-1H-imidazo[4,5-c]quinolin-7-yl]prop-2-enoate as starting material and isolated (21 mg, 34%) as white solid; LC-MS (UV peak area, ESI) 93%, 456.4 ($MH^+$).

Example 8

Ethyl 3-(4-amino-1-(2-(2-aminoethoxy)-2-methylpropyl)-2-(ethoxymethyl)-1H-imidazo[4,5-c]quinolin-7-yl)propanoate hydrochloride a) Ethyl 3-[1-[2-[2-(tert-butoxycarbonylamino)ethoxy]-2-methylpropyl]-2-(ethoxymethyl)-4-(tritylamino)-1H-imidazo[4,5-c]quinolin-7-yl]propanoate

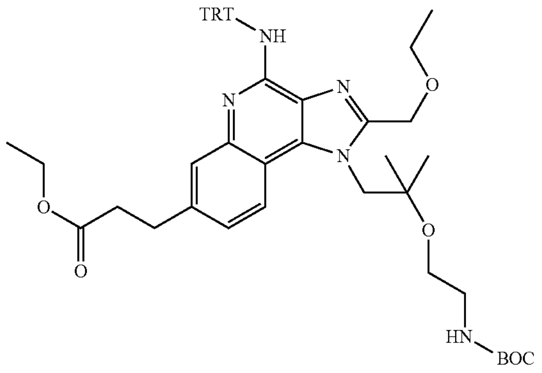

Palladium on carbon 10% (100 mg, 940 μmol) in ethanol (10 mL) was added to a suspension of (E)-ethyl 3-(1-(2-(2-(tert-butoxycarbonylamino)ethoxy)-2-methylpropyl)-2-(ethoxymethyl)-4-(tritylamino)-1H-imidazo[4,5-c]quinolin-7-yl)acrylate (280 mg, 351 μmol) in ethyl acetate (30 mL). The mixture was stirred for 6 h in a hydrogen atmosphere at room temperature, filtered and solvent was removed in vacuo. The residue was purified by flash chromatography (silica gel-$NH_2$, 0% to 100% ethyl acetate in heptane) to give the title compound (0.163 g, 58%) as white solid; LC-MS (UV peak area, ESI) 74%, 800.5 ($MH^+$).

b) Ethyl 3-(4-amino-1-(2-(2-aminoethoxy)-2-methylpropyl)-2-(ethoxymethyl)-1H-imidazo[4,5-c]quinolin-7-yl) propanoate hydrochloride

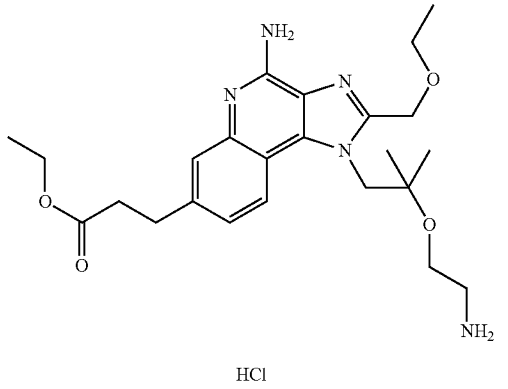 [SMILES: CCOCc1nc2c(N)nc3cc(CCC(=O)OCC)ccc3c2n1CC(C)(C)OCCN ; Cl]

The title compound was synthesized in analogy to Example 1c, using ethyl 3-[1-[2-[2-(tert-butoxycarbonylamino)ethoxy]-2-methylpropyl]-2-(ethoxymethyl)-4-(tritylamino)-1H-imidazo[4,5-c]quinolin-7-yl]propanoate as starting material and isolated (15 mg, 56%) as white solid; LC-MS (UV peak area, ESI) 93%, 458.4 ($MH^+$).

Example 9

Ethyl 3-(4-amino-1-(2-(2-aminoacetoxy)-2-methylpropyl)-2-(ethoxymethyl)-1H-imidazo[4,5-c]quinolin-7-yl)propanoate a) Ethyl 3-[4-[bis(benzyloxycarbonyl)amino]-2-(ethoxymethyl)-1-(2-hydroxy-2-methylpropyl)-1H-imidazo[4,5-c]quinolin-7-yl]propanoate

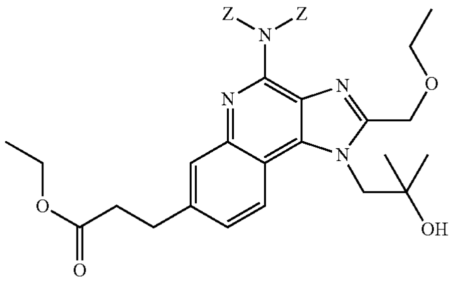

To a suspension of ethyl 3-(4-amino-2-(ethoxymethyl)-1-(2-hydroxy-2-methylpropyl)-1H-imidazo[4,5-c]quinolin-7-yl)propanoate hydrochloride (300 mg, 665 μmol) DMAP (15 mg, 123 μmol) and DIEA (1.86 ml, 10.6 mmol) in dichloromethane (6 mL), benzyl chloroformate (380 μl, 2.66 mmol) was added. The reaction mixture stirred at room temperature for 20 h, more benzyl chloroformate (908 60 μl, 5.32 mmol) was added and stirring continued for another 6 h. Afterwards the mixture was poured into dichloromethane (50 mL), extracted with HCl (1M, 20 mL) and water (20 mL). The aqueous layer was extracted with dichloromethane (50 mL), organic phases were combined, dried with $MgSO_4$ and concentrated in vacuo. The residue was purified by flash chromatography (silica gel, 0% to 100% ethyl acetate in heptane) to give the title compound (0.459 g, quant.) as colorless oil; LC-MS (UV peak area, ESI) 86%, 683.5 ($MH^+$).

b) Ethyl 3-[4-(benzyloxycarbonylamino)-1-[2-[2-(dibenzylamino)acetyl]oxy-2-methylpropyl]-2-(ethoxymethyl)-1H-imidazo[4,5-c]quinolin-7-yl]propanoate

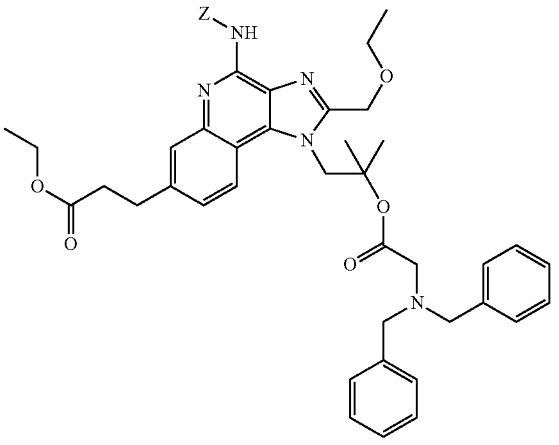

To a suspension of ethyl 3-(4-(bis(benzyloxycarbonyl) amino)-2-(ethoxymethyl)-1-(2-hydroxy-2-methylpropyl)-1H-imidazo[4,5-c]quinolin-7-yl)propanoate (300 mg, 439 μmol), 2-(dibenzylamino)acetic acid (337 mg, 1.32 mmol)

and DMAP (107 mg, 879 μmol) in dichloromethane (4 mL) was added 1-ethyl-3-(3-dimethylaminopropyl)carbodiimide (253 mg, 1.32 mmol) and molecular sieves (300 mg). After 1 h stirring at room temperature starting materials had dissolved, stirring at room temperature continued for 6 h and the mixture was left standing over the weekend. The residue was diluted with dichloromethane (50 mL) and washed with HCl (1 M, 20 mL) and water (20 mL). The aqueous phase was extracted with dichloromethane (50 mL), organic phases were combined, dried with $MgSO_4$ and concentrated in vacuo. The residue was purified by flash chromatography (silica gel, 0% to 100% ethyl acetate in heptane) to give the title compound (182 mg, 52%) as light yellow oil; LC-MS (UV peak area, ESI) 98%, 784.6 ($MH^+$).

c) Ethyl 3-(4-amino-1-(2-(2-aminoacetoxy)-2-methylpropyl)-2-(ethoxymethyl)-1H-imidazo[4,5-c]quinolin-7-yl) propanoate

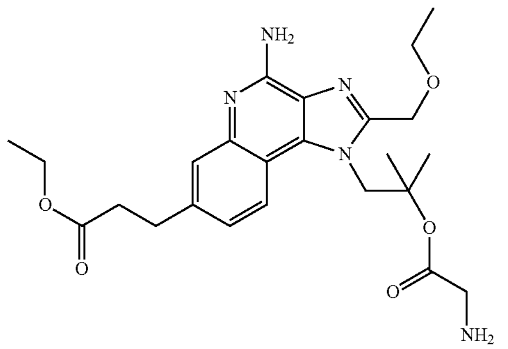 [SMILES: CCOCc1nc2c(N)nc3cc(CCC(=O)OCC)ccc3c2n1CC(C)(C)OC(=O)CN]

Ethyl 3-(4-(benzyloxycarbonylamino)-1-(2-(2-(dibenzylamino)acetoxy)-2-methylpropyl)-2-(ethoxymethyl)-1H-imidazo[4,5-c]quinolin-7-yl)propanoate (182 mg, 232 μmol) was combined with ethyl acetate (20 mL) to give a light yellow solution. Palladium on carbon 10% (600 mg, 232 μmol) was added and the mixture was stirred for 20 h at room temperature under $H_2$. Afterwards the mixture was filtered through celite® and concentrated in vacuo. The crude material was purified by flash chromatography (silica gel, 20 g, 0% to 30% methanol in THF) to 27 mg of an impure sample that was further purified by preparative HPLC to give the title compound (6 mg, 5%) as light yellow oil; LC-MS (UV peak area, ESI) 79%, 516.5 ($MHCOO^-$).

Example 10

1-(2-(2-Aminoethoxy)-2-methylpropyl)-2-pentyl-1H-imidazo[4,5-c]quinolin-4-amine a) 2-Methyl-1-(2-pentyl-1H-imidazo[4,5-c]quinolin-1-yl)propan-2-ol

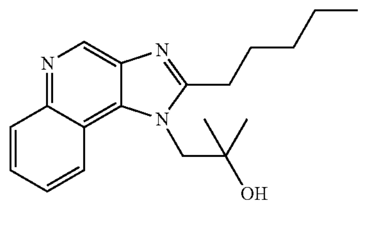 [SMILES: CCCCCc1nc2cnc3ccccc3c2n1CC(C)(C)O]

To a solution of 1-(3-aminoquinolin-4-ylamino)-2-methylpropan-2-ol (CAN 129655-59-0, 0.94 g, 4.06 mmol) in dichloromethane (9.5 mL) in an inert atmosphere was added dropwise with stirring at room temperature over a period of 6 min a solution of hexanoyl chloride (422 μl, 4.47 mmol) in dichloromethane (6.4 mL). After 3 h additional hexanoyl chloride (192 μl, 2.03 mmol) was added and stirring continued for another hour and finally the mixture was concentrated in vacuo. The residue was re-dissolved in ethanol (13.5 mL) and, after addition of sodiumhydroxide solution (1 M, 10.8 mL) the mixture was heated with stirring in argon to 90° C. After 75 min the mixture was allowed to cool to room temperature and concentrated in vacuo. The residue was stirred with ethyl acetate (30 mL) and water (5 mL) dried by filtration over ChemElut® and ethyl acetate was removed in vacuo. The residue was purified by flash chromatography (silica gel-$NH_2$, 0% to 100% ethyl acetate in heptane) to give the title compound (747 mg, 89%) as yellow oil; LC-MS (UV peak area, ESI) 95%, 312.2 ($MH^+$).

b) 2-Methyl-1-(5-oxido-2-pentyl-1H-imidazo[4,5-c]quinolin-5-ium-1-yl)propan-2-ol

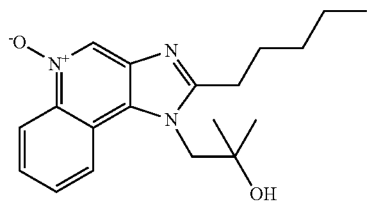

To a solution of 2-methyl-1-(2-pentyl-1H-imidazo[4,5-c]quinolin-1-yl)propan-2-ol (457 mg, 1.36 mmol) in dichloromethane (21.2 mL) was added with stirring 3-chloroperoxybenzoic acid (283 mg, 1.64 mmol) in one portion. The reaction mixture was stirred for 16 h at room temperature. Afterwards the mixture was partitioned between cold dichloromethane (50 mL) and sodium hydroxide solution (1 M, 20 mL). The organic phase was washed with cold water (20 mL) and brine (20 mL) and aqueous phases were extracted with dichloromethane (2×50 mL). All organic phases were combined, dried with $MgSO_4$, filtered and concentrated in vacuo, The residue was purified by flash chromatography (silica gel, 0% to 20% methanol in dichloromethane) to give the title compound (360 mg, 80%) as light yellow solid; LC-MS (UV peak area, ESI) 99%, 328.2 ($MH^+$).

c) 1-(4-Amino-2-pentyl-1H-imidazo[4,5-c]quinolin-1-yl)-2-methyl-propan-2-ol

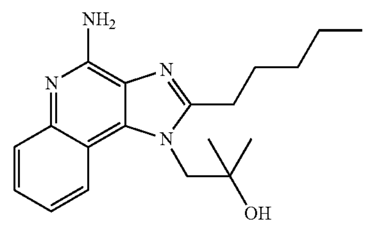 [SMILES: CCCCCc1nc2c(N)nc3ccccc3c2n1CC(C)(C)O]

To a solution of 2-methyl-1-(5-oxido-2-pentyl-1H-imidazo[4,5-c]quinolin-5-ium-1-yl)propan-2-ol (353 mg, 1.08 mmol) in anhydrous dichloromethane (47.6 mL) was added benzoyl isocyanate (90%, 286 μl, 2.05 mmol) with stirring in argon atmosphere at room temperature. The reaction mixture was stirred at reflux temperature for 35 min. The mixture was then concentrated in vacuo. The residue was then combined with anhydrous methanol (17.0 mL) to give a white suspension. Sodium methoxide solution in methanol (1.7 ml, 9.16 mmol) was added and the mixture was stirred for 1 h at 70° C. Afterwards the mixture was cooled to room temperature and solvents were removed in vacuo. The residue was partitioned between ethyl acetate (30 mL) and water (15 mL), dried by passage through a ChemElut® cartridge and concentrated in vacuo. The residue was purified by flash chromatography (silica gel, 0% to 10% methanol in dichloromethane) to give the title compound (221 mg, 61%) as white solid; LC-MS (UV peak area, ESI) 98%, 327.2185 ($MH^+$).

d) 2-Methyl-1-[2-pentyl-4-(tritylamino)-1H-imidazo[4,5-c]quinolin-1-yl]propan-2-ol

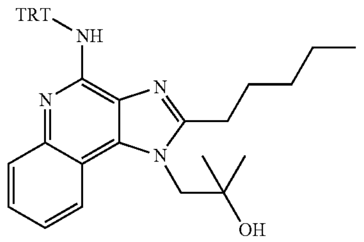

The title compound was synthesized in analogy to Example 1a, using 1-(4-amino-2-pentyl-1H-imidazo[4,5-c]quinolin-1-yl)-2-methyl-propan-2-ol as starting material and isolated (230 mg, 71%) as white crystalline solid; LC-MS (UV peak area, ESI) 99%, 569.3 ($MH^+$).

f) tert-Butyl N-[2-[1,1-dimethyl-2-[2-pentyl-4-(tritylamino)-1H-imidazo[4,5-c]quinolin-1-yl]ethoxy]ethyl]carbamate

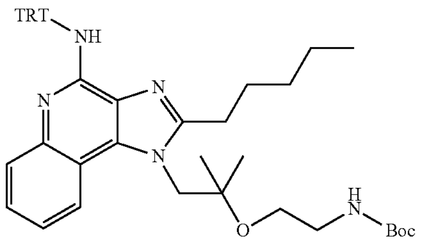

The title compound was synthesized in analogy to Example 1b, using 2-methyl-1-[2-pentyl-4-(tritylamino)-1H-imidazo[4,5-c]quinolin-1-yl]propan-2-ol as starting material and isolated (306 mg, quant.) as light yellow oil; LC-MS (UV peak area, ESI) 53%, 712.2 ($MH^+$).

g) 1-(2-(2-Aminoethoxy)-2-methylpropyl)-2-pentyl-1H-imidazo[4,5-c]quinolin-4-amine

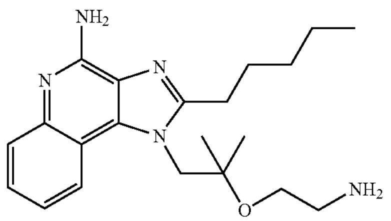 [SMILES: CCCCCc1nc2c(N)nc3ccccc3c2n1CC(C)(C)OCCN]

The title compound was synthesized in analogy to Example 1c, using tert-butyl N-[2-[1,1-dimethyl-2-[2-pentyl-4-(tritylamino)-1H-imidazo[4,5-c]quinolin-1-yl]ethoxy]ethyl]carbamate as starting material and isolated (30 mg, 36%) as white solid; LC-MS (UV peak area, ESI) 98%, 370.2622 ($MH^+$).

Example 11

1-(2-(2-Aminoethoxy)-2-methylpropyl)-7-bromo-2-(ethoxymethyl)-1H-imidazo[4,5-c]quinolin-4-amine hydrochloride a) 1-[7-Bromo-2-(ethoxymethyl)-4-(tritylamino)-1H-imidazo[4,5-c]quinolin-1-yl]-2-methylpropan-2-ol

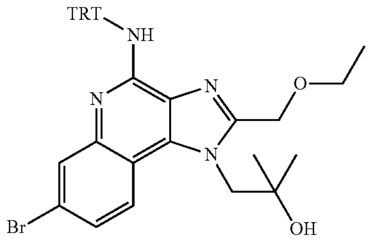

The title compound was synthesized in analogy to Example 1a, using 1-(4-amino-7 bromo-2-(ethoxymethyl)-1H-imidazo[4,5-c]quinolin-1-yl)-2-methylpropan-2-ol as starting material and isolated (100 mg, 88%) as light brown crystalline solid; LC-MS (UV peak area, ESI) 95%, 637.3 (MH+).

b) tert-Butyl N-[2-[2-[7-bromo-2-(ethoxymethyl)-4-(tritylamino)-1H-imidazo[4,5-c]quinolin-1-yl]-1,1-dimethyl-ethoxy]ethyl]carbamate

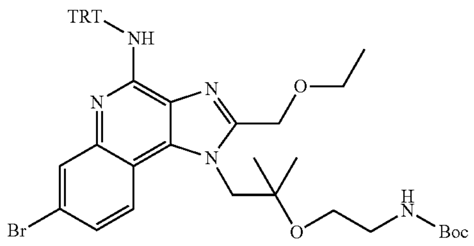

The title compound was synthesized in analogy to Example 1b, using 1-[7-bromo-2-(ethoxymethyl)-4-(tritylamino)-1H-imidazo[4,5-c]quinolin-1-yl]-2-methylpropan-2-ol as starting material and isolated (20 mg, 44%) as white solid which was used without further purification in the next step.

c) 1-(2-(2-Aminoethoxy)-2-methylpropyl)-7-bromo-2-(ethoxymethyl)-1H-imidazo[4,5-c]quinolin-4-amine hydrochloride

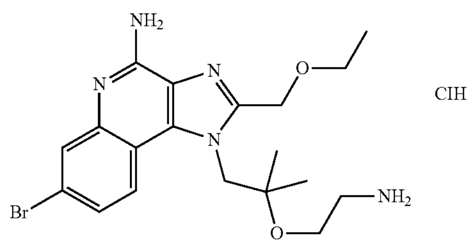 [SMILES: CCOCc1nc2c(N)nc3cc(Br)ccc3c2n1CC(C)(C)OCCN ; "CIH"]

The title compound was synthesized in analogy to Example 1c, using tent-butyl N-[2-[2-[7-bromo-2-(ethoxymethyl)-4-(tritylamino)-1H-imidazo[4,5-c]quinolin-1-yl]-1,1-dimethyl-ethoxy]ethyl]carbamate as starting material and isolated (7 mg, 58%) as white solid; LC-MS (UV peak area, ESI) 99%, 438.2 (MH+).

What is claimed is:

1. A method of treating cancer, an autoimmune disease or infectious disease, the method comprising administering to a patient in need thereof a therapeutically effective amount of a compound of formula I

I

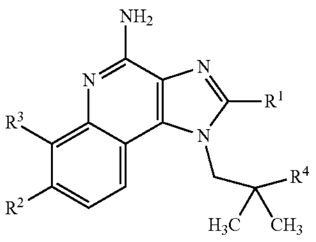

wherein $R^1$ is $C_{1-7}$-alkyl or $C_{1-7}$-alkoxy-$C_{1-7}$-alkyl;

$R^2$ is selected from the group consisting of hydrogen, halogen, hydroxyl, hydroxy-$C_{1-7}$-alkyl, alkoxy-$C_{1-7}$-alkyl, carboxyl, carboxyl-$C_{1-7}$-alkyl, carboxyl-$C_{2-7}$-alkenyl, aminocarbonyl-$C_{1-7}$-alkyl, aminocarbonyl-$C_{2-7}$-alkenyl, $C_{1-7}$-alkylamino-carbonyl-$C_{1-7}$-alkyl, $C_{1-7}$-alkylamino-carbonyl-$C_{2-7}$-alkenyl, $C_{1-7}$-alkoxycarbonyl-$C_{1-7}$-alkyl, $C_{1-7}$-alkoxycarbonyl-$C_{2-7}$-alkenyl, $C_{1-7}$-alkyl-sulfonyl-$C_{1-7}$-alkyl, sulfamoyl-$C_{1-7}$-alkyl, $C_{1-7}$-alkyl-sulfamoyl-$C_{1-7}$-alkyl, phenyl, said phenyl being unsubstituted or substituted with one, two or three groups selected from the group consisting of $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro, and phenoxy, said phenoxy group being unsubstituted or substituted with one, two or three groups selected from the group consisting of $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkyl-sulfonyl, hydroxy-$C_{1-7}$-alkylsulfonyl, $C_{1-7}$-alkoxy-$C_{1-7}$-alkylsulfonyl, carboxyl-$C_{1,7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro;

$R^3$ is hydrogen or halogen;

$R^4$ is selected from the group consisting of $—O—(CH_2)_m$-$NHR^5$, and $—O—(CO)—(CH_2)_n$-$NHR^6$, wherein m is selected from 1, 2 or 3, n is selected from 1 or 2, $R^5$ is selected from the group consisting of hydrogen, hydroxy-$C_{1-7}$-alkyl, amino-$C_{1-7}$-alkyl, $C_{1-7}$-alkyl-carbonyl, phenylcarbonyl, heteroarylcarbonyl, carboxyl, carboxyl-$C_{1-7}$-alkyl and $C_{1-7}$- alkoxy-carbonyl-amino-$C_{1-7}$-alkyl-carbonyl, and $R^6$ is selected from the group consisting of hydrogen, hydroxy-$C_{1-7}$-alkyl, amino-$C_{1-7}$-alkyl, $C_{1-7}$-alkyl-carbonyl, phenylcarbonyl, heteroarylcarbonyl, carboxyl, carboxyl-$C_{1-7}$-alkyl and $C_{1-7}$- alkoxy-carbonyl-amino-$C_{1-7}$-alkyl-carbonyl, or a pharmaceutically acceptable salt thereof.

2. The method of claim 1 wherein the compound of formula I is selected from the group consisting of 1-(2-(2-aminoethoxy)-2-methylpropyl)-2-(ethoxymethyl)-1H-imidazo[4,5-c]quinolin-4-amine, 1-(4-amino-2-(ethoxymethyl)-1H-imidazo[4,5-c]quinolin-1-yl)-2-methylpropan-2-yl 2-aminoacetate, N-(2-(1-(4-amino-2-(ethoxymethyl)-1H-imidazo[4,5-c]quinolin-1-yl)-2-methylpropan-2-yloxy)ethyl)nicotinamide, N-(2-(1-(4-amino-2-(ethoxymethyl)-1H-imidazo[4,5-c]quinolin-1-yl)-2-methylpropan-2-yloxy)ethyl)acetamide, 3-(2-(1-(4-amino-2-(ethoxymethyl)-1H-imidazo[4,5-c]quinolin-1-yl)-2-methylpropan-2-yloxy)ethylamino)propan-1-ol, tert-butyl 6-(2-(1-(4-amino-2-(ethoxymethyl)-1H-imidazo[4,5-c]quinolin-1-yl)-2-methylpropan-2-yloxy)ethylamino)-6-oxohexylcarbamate, ethyl (E)-3-[4-amino-1-[2-(2-aminoethoxy)-2-methylpropyl]-2-(ethoxymethyl)-1H-imidazo[4,5-c]quinolin-7-yl]prop-2-enoate, ethyl 3-(4-amino-1-(2-(2-aminoethoxy)-2-methylpropyl)-2-(ethoxymethyl)-1H-imidazo[4,5-c]quinolin-7-yl)propanoate, ethyl 3-(4-amino-1-(2-(2-aminoacetoxy)-2-methylpropyl)-2-(ethoxymethyl)-1H-imidazo[4,5-c]quinolin-7-yl)propanoate, 1-(2-(2-aminoethoxy)-2-methylpropyl)-2-pentyl-1H-imidazo[4,5-c]quinolin-4-amine, and 1-(2-(2-aminoethoxy)-2-methylpropyl)-7-bromo-2-(ethoxymethyl)-1H-imidazo[4,5-c]quinolin-4-amine, or a pharmaceutically acceptable salt thereof.

3. The method of claim 1 wherein the compound of formula I is 1-(2-(2-aminoethoxy)-2-methylpropyl)-2-(ethoxymethyl)-1H-imidazo[4,5-c]quinolin-4-amine, or a pharmaceutically acceptable salt thereof.

4. The method of claim 1 wherein the compound of formula I is 1-(4-amino-2-(ethoxymethyl)-1H-imidazo[4,5-c]quinolin-1-yl)-2-methylpropan-2-yl 2-aminoacetate, or a pharmaceutically acceptable salt thereof.

5. The method of claim 1 wherein the compound of formula I is ethyl 3-(4-amino-1-(2-(2-aminoethoxy)-2-methylpropyl)-2-(ethoxymethyl)-1H-imidazo[4,5-c]quinolin-7-yl)propanoate, or a pharmaceutically acceptable salt thereof.

6. The method of any one of claims 1 to 5 wherein the cancer is bladder cancer, head and neck cancer, prostate cancer, colorectal cancer, kidney cancer, breast cancer, lung cancer, ovarian cancer, cervical cancer, pancreatic cancer, bowel cancer, colon cancer, stomach cancer, thyroid cancer, melanoma, brain cancer, leukemia, and Hodgkin's or non-Hodgkin's lymphoma.

7. The method of any one of claims 1 to 5 wherein the autoimmune diseases is rheumatoid arthritis, Sjogren's syndrome, scleroderma, SLE, lupus nephritis, polymyositis/dermatomyositis, cryoglobulinemia, anti-phospholipid antibody syndrome, psoriatic arthritis, inflammatory bowel diseases, ulcerative colitis, Crohn's disease, autoimmune gastritis, pernicious anemia, autoimmune hepatitis, primary biliary cirrhosis, primary sclerosing cholangitis, celiac disease, ANCA-negative vasculitis, ANCA-associated vasculitis, Churg-Strauss vasculitis, Wegener's granulomatosis, microscopic polyangiitis, multiple sclerosis, opsoclonus myoclonus syndrome, myasthenia gravis, neuromyelitis optica, Parkinson's disease, Alzheimer's disease, glomerulonephritis, Goodpasture's syndrome, Berger's disease, psoriasis, urticaria, hives, pemphigus vulgaris, bullous pemphigoid, and cutaneous lupus erythematosus, thrombocytopenic purpura, thrombotic thrombocytopenic purpura, post-transfusion purpura, autoimmune hemolytic anemia, atherosclerosis, uveitis, Behcet's disease, Raynaud's syndrome, insulin-dependent diabetes mellitus (IDDM), Addison's disease, Graves' disease, thyroiditis, food allergies, drug allergies, insect allergies, mastocytosis, eczema, or asthma.

8. The method any one of claims 1 to 5 wherein the infectious disease is human papilloma virus, genital warts, common warts, plantar warts, herpes simplex virus, molluscum contagiosum, hepatitis B virus (HBV), hepatitis C virus (HCV), Dengue virus, variola virus, human immunodeficiency virus (HIV), cytomegalovirus (CMV), varicella zoster virus (VZV), rhinovirus, enterovirus, adenovirus, coronavirus, influenza, mumps or parainfluenza.

9. The method of any one of claims 1 to 5 wherein the infectious disease is a bacterial, fungal or parasitic disease selected from *mycobacterium tuberculosis, mycobacterium avium, mycobacterium leprae*, chlamydia, candidiasis, aspergillosis, cryptococcal meningitis, Pneumocystis carnii, pneumonia, cryptosporidiosis, histoplasmosis, toxoplasmosis, trypanosome infection or leishmaniasis.

10. A process for the manufacture of a compound of formula I,

I

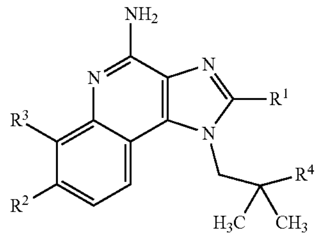

wherein $R^1$ is $C_{1-7}$-alkyl or $C_{1-7}$-alkoxy-$C_{1-7}$-alkyl;

$R^2$ is selected from the group consisting of hydrogen, halogen, hydroxyl, hydroxy-$C_{1-7}$-alkyl, alkoxy-$C_{1-7}$-alkyl, carboxyl, carboxyl-$C_{1-7}$-alkyl, carboxyl-$C_{2-7}$-alkenyl, aminocarbonyl-$C_{1-7}$-alkyl, aminocarbonyl-$C_{2-7}$-alkenyl, $C_{1-7}$-alkylamino-carbonyl-$C_{1-7}$-alkyl, $C_{1-7}$-alkylamino-carbonyl-$C_{2-7}$-alkenyl, $C_{1-7}$-alkoxy-carbonyl-$C_{1-7}$-alkyl, $C_{1-7}$-alkoxycarbonyl-$C_{2-7}$-alkenyl, $C_{1-7}$-alkyl-sulfonyl-$C_{1-7}$-alkyl, sulfamoyl-$C_{1-7}$-alkyl, $C_{1-7}$-alkyl-sulfamoyl-$C_{1-7}$-alkyl, phenyl, said phenyl being unsubstituted or substituted with one, two or three groups selected from the group consisting of $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro, and phenoxy, said phenoxy group being unsubstituted or substituted with one, two or three groups selected from the group consisting of $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkyl-sulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxy-carbonyl-$C_{1-7}$-alkylsulfonyl, amino, $C_{1-7}$-alkylamino, di-$C_{1-7}$-alkylamino and nitro;

$R^3$ is hydrogen or halogen;

$R^4$ is selected from the group consisting of $-O-(CH_2)_m-NHR^5$, and $-O-(CO)-(CH_2)_n-NHR^6$, wherein m is selected from 1, 2 or 3, n is selected from 1 or 2, $R^5$ is selected from the group consisting of hydrogen, hydroxy-$C_{1-7}$-alkyl, amino-$C_{1-7}$-alkyl, $C_{1-7}$-alkyl-carbonyl, phenylcarbonyl, heteroarylcarbonyl, carboxyl, carboxyl-$C_{1-7}$-alkyl and $C_{1-7}$- alkoxy-carbonyl-amino-$C_{1-7}$-alkyl-carbonyl, and $R^6$ is selected from the group consisting of hydrogen, hydroxy-$C_{1-7}$-alkyl, amino-$C_{1-7}$-alkyl, $C_{1-7}$-alkyl-carbonyl, phenylcarbonyl, heteroarylcarbonyl, carboxyl, carboxyl-$C_{1-7}$-alkyl and $C_1$-$_7$- alkoxy-carbonyl-amino-$C_{1-7}$-alkyl-carbonyl, or a pharmaceutically acceptable salt thereof, which process comprises:

a) reacting a compound of the formula II

II

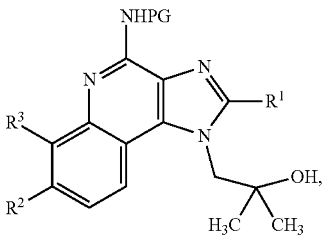

wherein PG is a protecting group, with a compound of the formula III

III

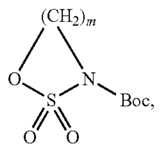

under basic conditions and removing the protecting groups PG and Boc under acidic conditions to obtain a compound of the formula I-a I-a

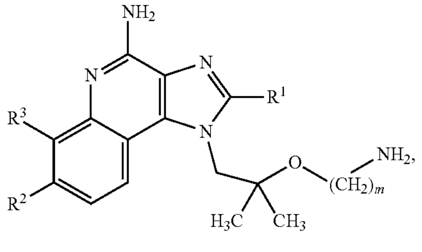

and optionally further coupling the compound of formula I-a with an alcohol or acid of the formula $R^5$—OH or an aldehyde of the formula $R^5$═O to obtain a compound of formula I-c, I-c

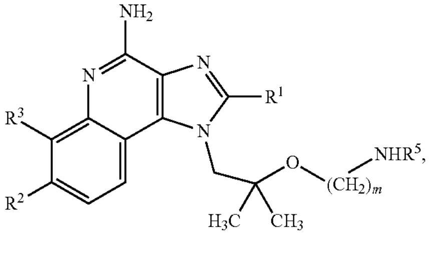

and, if desired, converting the compound obtained into a pharmaceutically acceptable salt; or b) reacting an compound of the formula II-a II-a

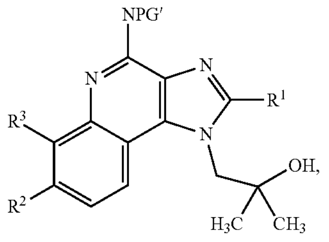

wherein PG' is a protecting group, with a carboxylic acid of the formula IV

IV

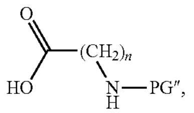

wherein PG" is a protecting group, in the presence of an esterification agent and removing the protecting groups PG' and PG" with a reducing agent to obtain a compound of the formula I-b, I-b

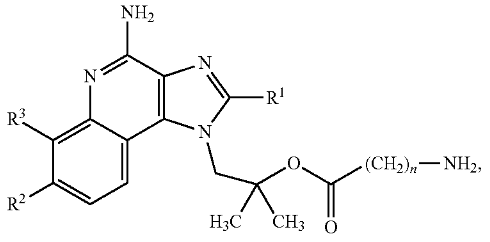

and optionally further coupling the compound of formula I-b with an alcohol or acid of the formula $R^6$—OH or and aldehyde of the formula $R^6$═O to obtain a compound of formula I-d, I-d

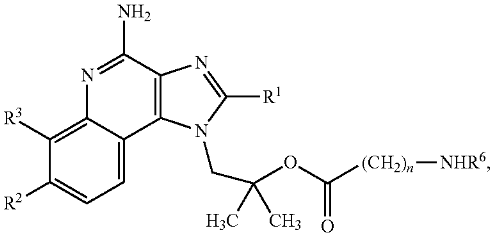

and, if desired, converting the compound obtained into a pharmaceutically acceptable salt.

11. The method of claim 10 wherein the compound of formula I is selected from the group consisting of 1-(2-(2-aminoethoxy)-2-methylpropyl)-2-(ethoxymethyl)-1H-imidazo[4,5-c]quinolin-4-amine, 1-(4-amino-2-(ethoxymethyl)-1H-imidazo[4,5-c]quinolin-1-yl)-2-methylpropan-2-yl 2-aminoacetate, N-(2-(1-(4-amino-2-(ethoxymethyl)-1H-imidazo[4,5-c]quinolin-1-yl)-2-methylpropan-2-yloxy)ethyl)nicotinamide, N-(2-(1-(4-amino-2-(ethoxymethyl)-1H-imidazo[4,5-c]quinolin-1-yl)-2-methylpropan-2-yloxy)ethyl)acetamide, 3-(2-(1-(4-amino-2-(ethoxymethyl)-1H-imidazo[4,5-c]quinolin-1-yl)-2-methylpropan-2-yloxy)ethylamino)propan-1-ol, tert-butyl 6-(2-(1-(4-amino-2-(ethoxymethyl)-1H-imidazo[4,5-c]quinolin-1-yl)-2-methylpropan-2-yloxy)ethylamino)-6-oxohexylcarbamate, ethyl (E)-3-[4-amino-1-[2-(2-aminoethoxy)-2-methylpropyl]-2-(ethoxymethyl)-1H-imidazo[4,5-c]quinolin-7-yl]prop-2-enoate, ethyl 3-(4-amino-1-(2-(2-aminoethoxy)-2-methylpropyl)-2-(ethoxymethyl)-1H-imidazo[4,5-c]quinolin-7-yl)propanoate, ethyl 3-(4-amino-1-(2-(2-aminoacetoxy)-2-methyl propyl)-2-(ethoxymethyl)-1H-imidazo[4,5-c]quinolin-7-yl)propanoate, 1-(2-(2-aminoethoxy)-2-methylpropyl)-2-pentyl-1H-imidazo[4,5-c]quinolin-4-amine, and 1-(2-(2-aminoethoxy)-2-methylpropyl)-7-bromo-2-(ethoxymethyl)-1H-imidazo[4,5-c]quinolin-4-amine, or a pharmaceutically acceptable salt thereof.

12. The method of claim 10 wherein the compound of formula I is 1-(2-(2-aminoethoxy)-2-methylpropyl)-2-

(ethoxymethyl)-1H-imidazo[4,5-c]quinolin-4-amine, or a pharmaceutically acceptable salt thereof.

13. The method of claim 10 wherein the compound of formula I is 1-(4-amino-2-(ethoxymethyl)-1H-imidazo[4,5-c]quinolin-1-yl)-2-methylpropan-2-yl 2-aminoacetate, or a pharmaceutically acceptable salt thereof.

14. The method of claim 10 wherein the compound of formula I is ethyl 3-(4-amino-1-(2-(2-aminoethoxy)-2-methylpropyl)-2-(ethoxymethyl)-1H-imidazo[4,5-c]quinolin-7-yl)propanoate, or a pharmaceutically acceptable salt thereof.

* * * * *